(12) United States Patent
Gao

(10) Patent No.: US 10,674,976 B2
(45) Date of Patent: Jun. 9, 2020

(54) IMAGING DEVICE AND MEDICAL APPARATUS

(71) Applicant: BEIJING NEUSOFT MEDICAL EQUIPMENT CO., LTD., Beijing (CN)

(72) Inventor: Shang Gao, Shenyang (CN)

(73) Assignee: BEIJING NEUSOFT MEDICAL EQUIPMENT CO., LTD., Beijing (CN)

( * ) Notice: Subject to any disclaimer, the term of this patent is extended or adjusted under 35 U.S.C. 154(b) by 0 days.

(21) Appl. No.: 16/144,876

(22) Filed: Sep. 27, 2018

(65) Prior Publication Data

US 2019/0090831 A1   Mar. 28, 2019

(30) Foreign Application Priority Data

Sep. 28, 2017   (CN) .......................... 2017 1 0899767

(51) Int. Cl.
  *A61B 6/00*   (2006.01)
  *A61B 6/03*   (2006.01)
  *A61B 6/04*   (2006.01)
(52) U.S. Cl.
  CPC ............ *A61B 6/4447* (2013.01); *A61B 6/035* (2013.01); *A61B 6/4405* (2013.01);
  (Continued)
(58) Field of Classification Search
  None
  See application file for complete search history.

(56) References Cited

U.S. PATENT DOCUMENTS

| 6,203,196 B1 * | 3/2001 | Meyer ................. A61B 6/4441 378/197 |
| 2011/0216199 A1 * | 9/2011 | Trevino .................. B60D 1/36 348/148 |

(Continued)

FOREIGN PATENT DOCUMENTS

| CN | 1353593 A | 6/2002 |
| CN | 101209209 A | 7/2008 |

(Continued)

OTHER PUBLICATIONS

United States Patent and Trademark Office, Office Action Issued in U.S. Appl. No. 16/144,843, dated Dec. 5, 2019, 12 pages.

(Continued)

*Primary Examiner* — Hoon K Song
(74) *Attorney, Agent, or Firm* — McCoy Russell LLP

(57) ABSTRACT

Imaging devices and medical apparatuses are provided. The imaging device comprises a first cantilever, a second cantilever and an aligning and locking device where the second cantilever is separably connected with the first cantilever, and the aligning and locking device is provided at a connection of the first cantilever and the second cantilever and comprises a positioning groove, a positioning block and a locking member. The positioning groove is concavely provided on one of the first cantilever and the second cantilever and the positioning block is convexly provided on the other and extendable into the positioning groove to cooperate with the positioning groove for positioning. A locking groove is concavely provided in the positioning block. The locking member is movably provided in the cantilever on which the positioning groove is provided, and may insert into the locking groove to cooperate with the locking groove for locking.

17 Claims, 21 Drawing Sheets

(52) U.S. Cl.
CPC .......... *A61B 6/4411* (2013.01); *A61B 6/4441* (2013.01); *A61B 6/504* (2013.01); *A61B 6/505* (2013.01); *A61B 6/032* (2013.01); *A61B 6/04* (2013.01); *A61B 6/56* (2013.01); *G06T 2207/10081* (2013.01)

(56) References Cited

U.S. PATENT DOCUMENTS

| | | | | |
|---|---|---|---|---|
| 2014/0346746 | A1* | 11/2014 | Li | B62B 9/085 280/47.38 |
| 2016/0270749 | A1 | 9/2016 | Patwardhan | |

FOREIGN PATENT DOCUMENTS

| | | |
|---|---|---|
| CN | 101553960 A | 10/2009 |
| CN | 102877767 A | 1/2013 |
| CN | 103287475 A | 9/2013 |
| CN | 104379060 A | 2/2015 |
| CN | 204520732 U | 8/2015 |
| CN | 204600518 U | 9/2015 |
| CN | 106144786 A | 11/2016 |
| CN | 107126214 A | 9/2017 |
| JP | 2002165788 A | 6/2002 |
| JP | 2004223059 A | 8/2004 |

OTHER PUBLICATIONS

United States Patent and Trademark Office, Office Action Issued in U.S. Appl. No. 16/144,821, dated Dec. 6, 2019, 7 pages.

State Intellectual Property Office of the People's Republic of China, Office Action and Search Report Issued in Application No. 201710898422.9, dated Feb. 6, 2020, 22 pages. (Submitted with Partial Translation).

State Intellectual Property Office of the People's Republic of China, Office Action and Search Report Issued in Application No. 201710901631.4, dated Mar. 13, 2020, 20 pages (Submitted with Machine Translation).

State Intellectual Property Office of the People's Republic of China, Office Action and Search Report Issued in Application No. 201710899767.6, dated Apr. 8, 2020, 19 pages. (Submitted with Machine Translation).

* cited by examiner

IMAGING DEVICE AND MEDICAL APPARATUS

CROSS REFERENCE TO RELATED APPLICATIONS

The present application claims priority to Chinese Patent Application No. 201710899767.6 entitled "IMAGING DEVICE AND MEDICAL APPARATUS," and filed on Sep. 28, 2017. The entire contents of the above-mentioned application are incorporated herein by reference for all purposes.

BACKGROUND

An angiography machine is a real-time X-ray medical imaging device that also provides a platform for interventional treatment. The angiography machine can perform imaging of blood vessels in various parts of a whole body such as heart, brain, aorta, abdominal organs, pelvic cavity, limbs and the like, which helps with diagnosis of vascular lesions, tumor lesions and the like of the above different regions. Besides, the angiography machine can perform interventional treatment of lesions in different regions of the whole body, such as vascular embolization of liver cancer, perfusion chemotherapy of lung cancer, embolization of cerebral aneurysm, embolization of cerebral arteriovenous malformation, balloon dilatation and stenting of coronary artery stenosis, congenital heart disease atrial septal defect and ductus arteriosus occlusion, balloon dilatation of mitral and pulmonary stenosis, biliary and esophageal dilation and stenting, different percutaneous biopsy and drainage and other advanced interventional procedures.

The angiography machine can perform imaging at different angles and in different positions in cooperation with a scanning bed system by using a rotatable cantilever loaded with an X-ray source and a detector, and a bracket capable of rotating or translating the cantilever.

NEUSOFT MEDICAL SYSTEMS CO., LTD. (NMS), founded in 1998 with its world headquarters in China, is a leading supplier of medical equipment, medical IT solutions, and healthcare services. NMS supplies medical equipment with a wide portfolio, including CT, Magnetic Resonance Imaging (MRI), digital X-ray machine, ultrasound, Positron Emission Tomography (PET), Linear Accelerator (LINAC), and biochemistry analyser. Currently, NMS' products are exported to over 60 countries and regions around the globe, serving more than 5,000 renowned customers. NMS's latest successful developments, such as 128 Multi-Slice CT Scanner System, Superconducting MRI, LINAC, and PET products, have led China to become a global high-end medical equipment producer. As an integrated supplier with extensive experience in large medical equipment, NMS has been committed to the study of avoiding secondary potential harm caused by excessive X-ray irradiation to the subject during the CT scanning process.

DETAILED DESCRIPTION

Figure 1:
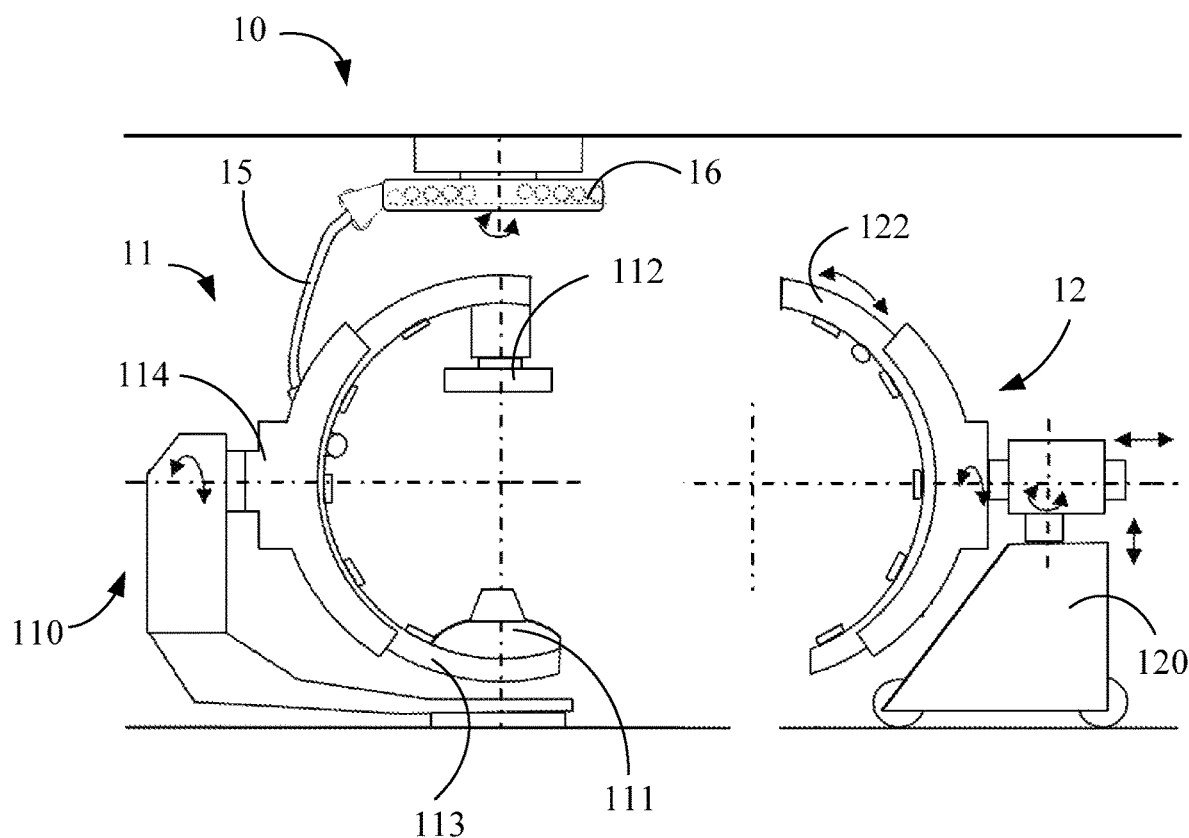
FIG. 1 is a schematic diagram illustrating an imaging system 10 according to an example of the present disclosure, where a first imaging device and a second gantry of the imaging system 10 are separated.

According to an example of the present disclosure, an imaging device may include a first cantilever, a second cantilever and an aligning and locking device. The second cantilever is separably connected with the first cantilever. The aligning and locking device is provided at a connection of the first cantilever and the second cantilever. The aligning and locking apparatus includes a positioning groove, a positioning block and a locking member. The positioning groove is concavely provided on one of the first cantilever and the second cantilever. The positioning block is convexly provided on the other one of the first cantilever and the second cantilever and may protrude into the positioning groove to cooperate with the positioning groove for positioning. The positioning block is concavely provided with a locking groove. The locking member is movably provided in the one of the first cantilever and the second cantilever where the positioning groove is located and may be inserted into the locking groove to cooperate with the locking groove for locking. In the present disclosure, the first cantilever and the second cantilever are aligned and locked together by the aligning and locking device, so that the first cantilever and the second cantilever are firmly combined.

According to an example of the present disclosure, a medical apparatus may include a first component, a second component and an aligning and locking device. The second component is assembled with the first component. The aligning and locking device is provided at a connection of the first component and the second component for aligning and locking the second component to the first component. The aligning and locking device includes a positioning groove, a positioning block and a locking member. The positioning groove is concavely provided on the first component. The positioning block is convexly provided on the second component and may protrude into the positioning groove to cooperate with the positioning groove for positioning. The positioning block is concavely provided with a locking groove. The locking member is movably provided in the first component and may be inserted into the locking groove to cooperate with the locking groove for locking. In some examples, the first component may be one of the first cantilever and the second cantilever, and the second component may be the other one of the first cantilever and the second cantilever. In other examples, the first component may be another component in a device, and the second component may be a component assembled with the first component in the device.

According to an example of the present disclosure, an imaging device may include a first cantilever, a second cantilever and a locking member. The first cantilever includes a first guide wall. The second cantilever is separably connected with the first cantilever and includes a second guide wall adapted to cooperate with the first guide wall. The second guide wall is fitted to the first guide wall to guide connection of the first cantilever and the second cantilever. The locking member is inserted through the first guide wall and the second guide wall to lock the first cantilever and the second cantilever.

FIG. 1 is a schematic diagram illustrating a structure of an imaging system 10 according to an example of the present disclosure. The imaging system 10 may include a first imaging device 11 and a second gantry 12. The first imaging device 11 may include a first gantry 110, a first X-ray source 111 provided on the first gantry 110 and a first detector 112 that is opposed to the first X-ray source 111 and provided on the first gantry 110.

The first gantry 110 may include a first cantilever 113 provided with the first X-ray source 111 and the first detector 112 and a first bracket 114 carrying the first cantilever 113. The first cantilever 113 may be slidably connected with the first bracket 114. The first cantilever 113 may slide along an arc track relative to the first bracket 114. The first bracket 114 may drive the first cantilever 113 to rotate about a transverse axis, and the first bracket 114 may rotate about a longitudinal axis, so that a position and an angle of the first X-ray source 111 and the first detector 112 relative to a subject (not shown) may be adjusted, and a scan may be performed for a region of interest of the subject. In an illustrated example, the first cantilever 113 is a C-shaped cantilever. In other examples, the first cantilever 113 may be a G-shaped cantilever. In an illustrated example, the first bracket 114 is a floor-type bracket installed on the floor, and the first bracket 114 may rotate about the longitudinal axis relative to the floor.

The first X-ray source 111 may include an X-ray tube for emitting X-rays to a subject. In an example, the first X-ray source 111 may emit a cone-shaped X-ray beam. The first detector 112 may be used to detect attenuated X-rays passing through the subject. In an example, the first detector 112 may include a flat panel detector. The first cantilever 113 may drive the first X-ray source 111 and the first detector 112 to move by rotational movement for scanning a subject.

In an example, the first imaging device 11 may be used to execute a first imaging mode. In an example, the first imaging device 11 may include an angiography machine, and the first imaging mode may include an angiographic imaging mode. The first imaging device 11 may perform imaging for blood vessels of a subject according to the X-rays detected by the first detector 112, which is not limited hereto. In other examples, the first imaging device 11 may execute other imaging modes to perform scanning and imaging of other modes for the subject.

In an illustrated example, the first imaging device 11 may also include a cable 15 and a cable reel 16. In an example, the cable 15 is used to electrically connect the first X-ray source 111 and the first detector 112 to a bus, so as to electrically connect with devices such as a computer and a power source connected with the bus; and the cable 15 may transmit high-voltage electricity to the first X-ray source 111 and may transmit low-voltage electricity and signals. The cable reel 16 may receive the cable 15 and may reel the cable 15 in/out along with the movement of the first cantilever 113.

The second gantry 12 is separably connected with the first gantry 110 and may be combined with the first imaging device 11 to execute a second imaging mode. The second gantry 12 includes a second bracket 120 and a second cantilever 122 slidably connected with the second bracket 120. The second cantilever 122 is separably connected with the first cantilever 113. The second cantilever 122 may slide along an arc track relative to the second bracket 120, and the second bracket 120 may drive the second cantilever 122 to rotate about a transverse axis and a longitudinal axis. The second bracket 120 may also drive the second cantilever 122 to ascend and descend. In this way, a position and an angle of the second cantilever 122 may be adjusted to realize connection with the first cantilever 113. In other examples, a height and an angle of the second cantilever 122 may be adjusted according to a height and an angle of the first cantilever 113 of different first imaging devices 11 to realize connection with the different first imaging devices 11. In an illustrated example, the second gantry 12 is a floor type gantry and may be moveable. The connection or separation between the second gantry 12 and the first gantry 110 may be implemented by moving the second gantry 12.

Figure 2:
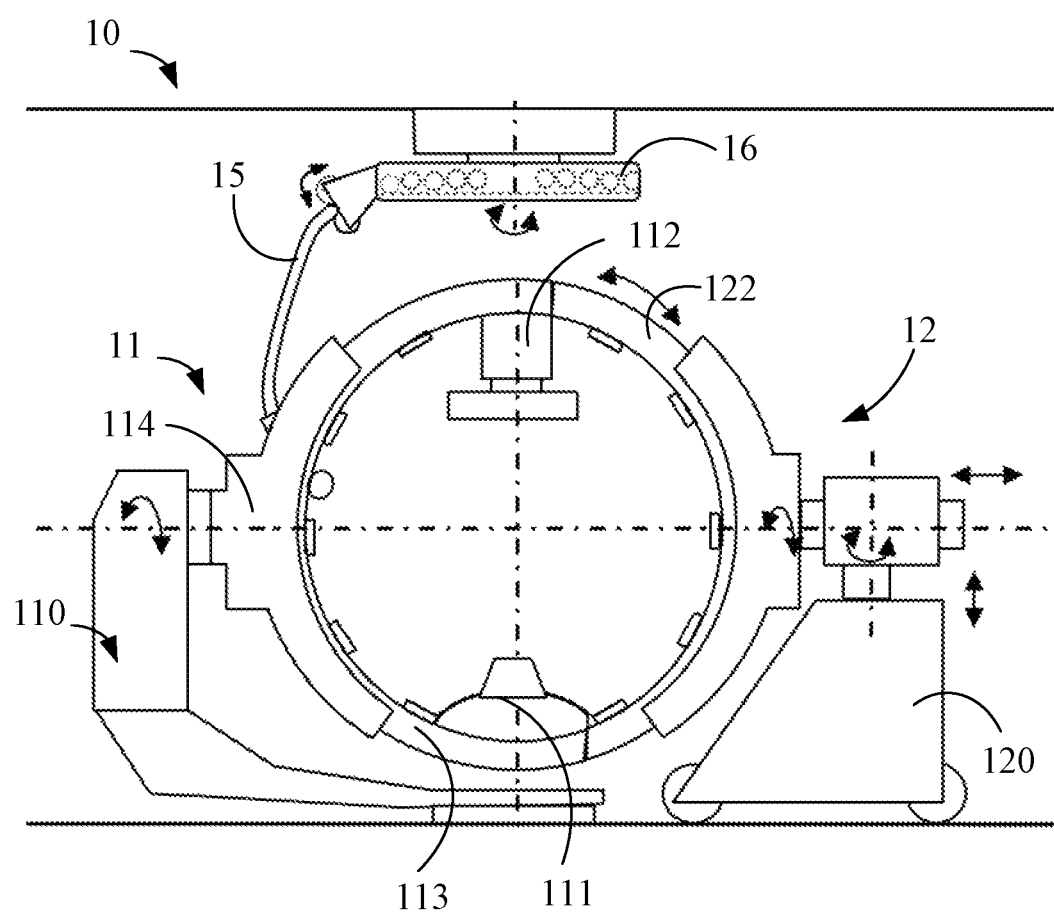
FIG. 2 is another schematic diagram illustrating the imaging system 10 shown in FIG. 1, where the first imaging device and the second gantry are combined together by connection.

FIG. 2 is a schematic diagram illustrating a combination of the first gantry 110 and the second gantry 12 shown in FIG. 1. The first imaging device 11 and the second gantry 12 may be combined to execute a second imaging mode. The second imaging device shown in FIG. 2 is used to execute the second imaging mode, and the second imaging device includes the first imaging device 11 and the second gantry 12. The second cantilever 122 of the second gantry 12 is connected with the first cantilever 113 of the first imaging device 11, and the two combined perform a rotation to drive the first X-ray source 111 and the first detector 112 to move. The first cantilever 113 and the second cantilever 122 may be connected to form a scanning ring of full rotation. The scanning ring may rotate an angle equal to or greater than 360 degrees, that is, the scanning ring may rotate one or more circles. In an example, the second cantilever 122 is a C-shaped cantilever smaller than a semicircle; the first cantilever 113 is a C-shaped cantilever greater than a semicircle.

In an example, the second imaging mode may include a Cone Beam Computed Tomography (CBCT) mode. In this example, the first X-ray source 111 and the first detector 112 may rotate 360 degrees or more to perform one or more circles of scan for a subject. A high-quality CT-like 2D image may be reconstructed using a CBCT algorithm according to a signal detected by the first detector 112 or a 3D image may be reconstructed based on the 2D image. Further, when a scan is performed, a CBCT scan is performed for whole body of a subject by moving a scanning bed carrying the subject, so that an image of the whole body of the subject may be obtained. In this way, a high-quality image may be obtained more easily before, during or after an interventional operation without performing a CT scan for the subject before the operation, thereby effectively reducing treatment time of diseases such as acute myocardial infarction or cerebral infarction. Also, it is not needed to move the subject to a CT room to receive a CT scan during or after an operation, effectively reducing radiation dose received by the subject. In other examples, the second imaging mode may include other imaging modes.

The first imaging device 11 of the imaging system 10 may function as an independent imaging device for executing the first imaging mode; the first imaging device 11 may also be combined with the second gantry 22 to obtain a second imaging device for executing the second imaging mode. The first imaging device may be changed into the second imaging device in the combination manner, and scan of one imaging mode or two imaging modes may be performed for the subject according to needs before, during or after an operation without moving the subject from one scanning room to another scanning room to receive scans of different modes, thereby effectively reducing treatment time. In addition, the first imaging device 11 may function as an independent imaging device, and may also be used as a part of the second imaging device. The first imaging device 11 may be used for different purposes. A desired imaging device may be obtained relatively easily according to an actual application to construct a hybrid operation room at a lower overall cost.

Figure 3:
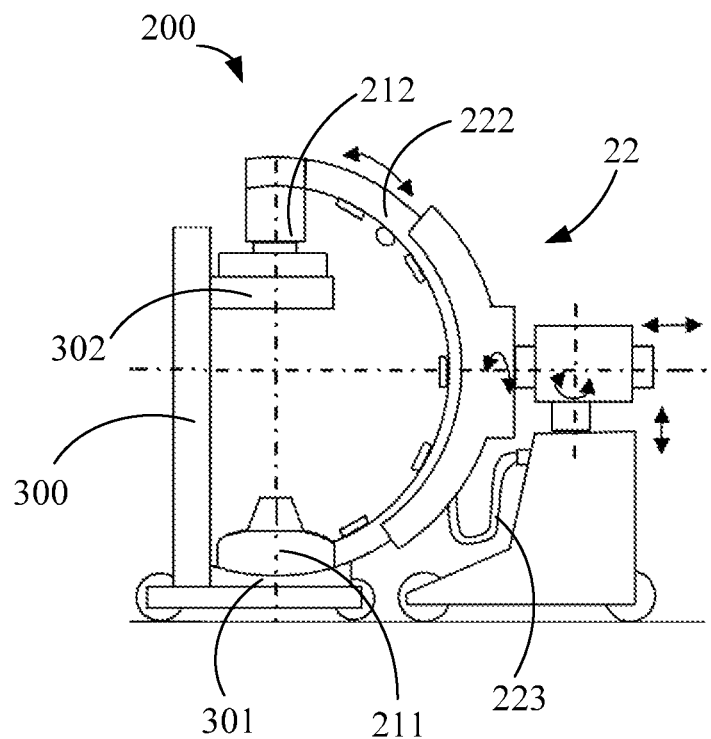
FIG. 3 is a schematic diagram illustrating a third imaging device 200 according to an example of the present disclosure.

FIG. 3 is a schematic diagram illustrating a third imaging device 200 according to an example of the present disclosure. The third imaging device 200 includes a second gantry 22, and a second X-ray source 211 and a second detector 212, both of which are detachably assembled on the second gantry 22 for executing a third imaging mode. The second gantry 22 shown in FIG. 3 is similar to the second gantry 12 shown in FIG. 1 and FIG. 2, and the second gantry 22 may be combined with the first imaging device 11 in FIG. 1 and FIG. 2 to execute the second imaging mode. When the second gantry 22 is combined with the first imaging device 11, electricity and signals may be transmitted by a cable 15 of the first imaging device 11. In FIG. 3, the second gantry 22 is separated from the first imaging device 11, and the second X-ray source 211 and the second detector 212 are assembled on the second gantry 22. In the example of FIG. 3, the second gantry 22 is provided with a cable 223, and the second X-ray source 211 and the second detector 212 are connected by the cable 223 to a bus or a control system or the like for transmitting electricity and signals.

In an example, the third imaging device 200 may be used to perform imaging for bones of a subject and may be used to assist in a surgery or a simple interventional operation, which is not limited hereto. In other examples, the third imaging device 200 may also be used as another angiography machine, or used to execute other scanning imaging modes according to an actual application. In an example, the second X-ray source 211 is similar to the first X-ray source 111 and may be used to emit a cone-shaped X-ray beam; the second detector 212 is similar to the first detector 112, and may include a flat panel detector.

In an example, the second X-ray source 211 and the second detector 212 may be placed on a carrying frame 300. The carrying frame 300 includes two carrying plates 301 and 302 separately provided at different heights to carry the second X-ray source 211 and the second detector 212, respectively. The second X-ray source 211 and the second detector 212 may be separated by the carrying plates 301 and 302 in a particular distance and the height of the carrying plates 301 and 302 correspond to two ends of the second cantilever 222. After the second X-ray source 211 and the second detector 212 are mounted on the second cantilever 222, the carrying frame 300 may be moved away to obtain a third imaging device 200.

Figure 4:
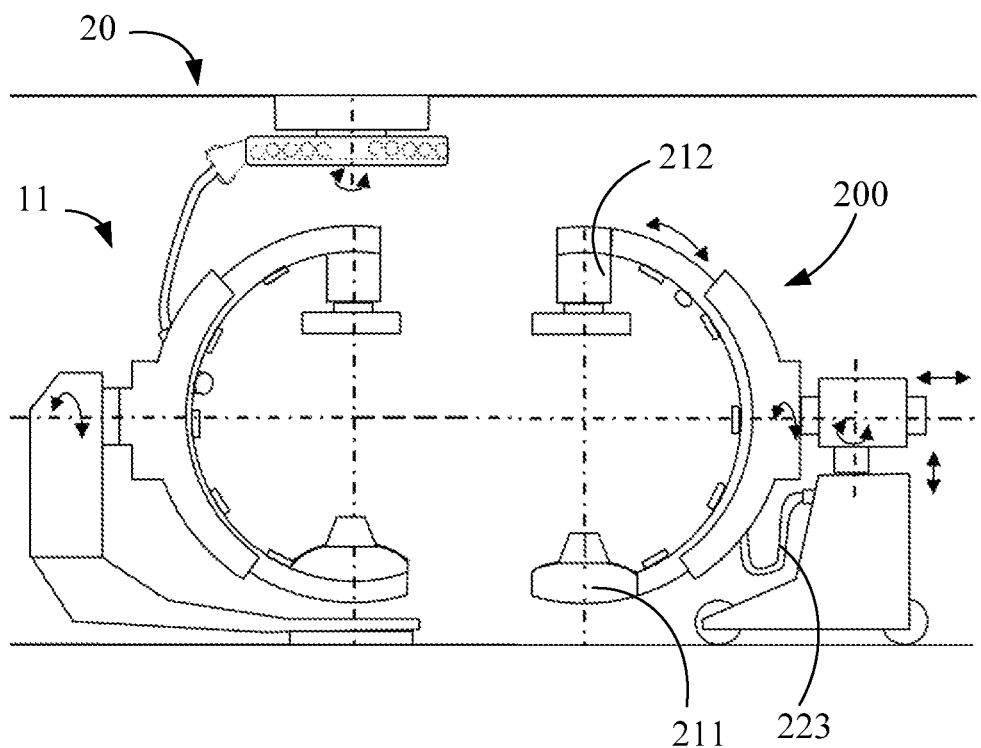
FIG. 4 is a schematic diagram illustrating an imaging system 20 according to an example of the present disclosure, where the imaging system 20 includes the third imaging device 200 shown in FIG. 3.

FIG. 4 is a schematic diagram illustrating an imaging system 20 according to another example of the present disclosure. The imaging system 20 shown in FIG. 4 is in a state that the first imaging device 11 and the third imaging device 200 operate independently. In this example, the first imaging device 11 of the imaging system 20 may be used as an independent imaging device for executing the first imaging mode; and the first imaging device 11 may be combined with the second gantry 22 to form the second imaging device for executing the second imaging mode. Besides, the second gantry 22 may be assembled with the second X-ray source 211 and the second detector 212 to form the third imaging device 200 for executing the third imaging mode. Thus, flexible combinations may be realized based on actual applications. One gantry may be used for different purposes to construct a hybrid operation room at a lower overall cost.

Figure 5:
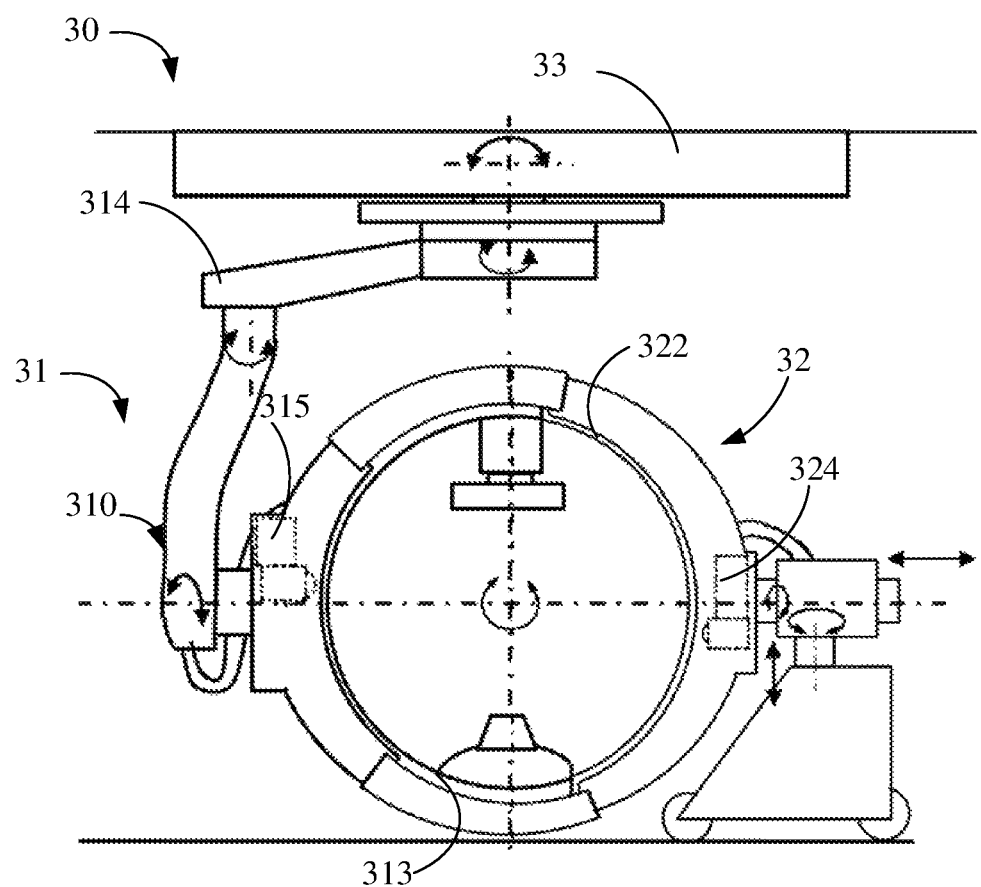
FIG. 5 is a schematic diagram illustrating an imaging system 30 according to an example of the present disclosure.

FIG. 5 is a schematic diagram illustrating an imaging system 30 according to another example of the present disclosure. The imaging system 30 shown in FIG. 5 mainly differs from the imaging system 10 shown in FIG. 1 in that: a first gantry 310 is a suspension gantry including a suspended first bracket 314 mounted on a ceiling, and the first bracket 314 may horizontally rotate relative to the ceiling. In some examples, the first bracket 314 may move along a guide rail 33 mounted on the ceiling.

In an illustrated example, the imaging system 30 includes a first motor 315 mounted on the first gantry 310 and a second motor 324 mounted on a second gantry 32. When the second gantry 32 and a first imaging device 31 are combined together, the first motor 315 and the second motor 324 may jointly drive a first cantilever 313 and a second cantilever 322 to move. In another example, the first motor 315 may drive the first cantilever 313 and the second cantilever 322 to move, and the second electric motor 324 may be omitted. In still another example, the first motor 315 and the second motor 324 are both provided on the first gantry 310 to jointly drive the first cantilever 313 and the second cantilever 322 which are combined to move. The motor driving manner in the above example may also be applied to the imaging system 10 shown in FIG. 1 to FIG. 3 and the imaging system 20 shown in FIG. 4.

Figure 6:
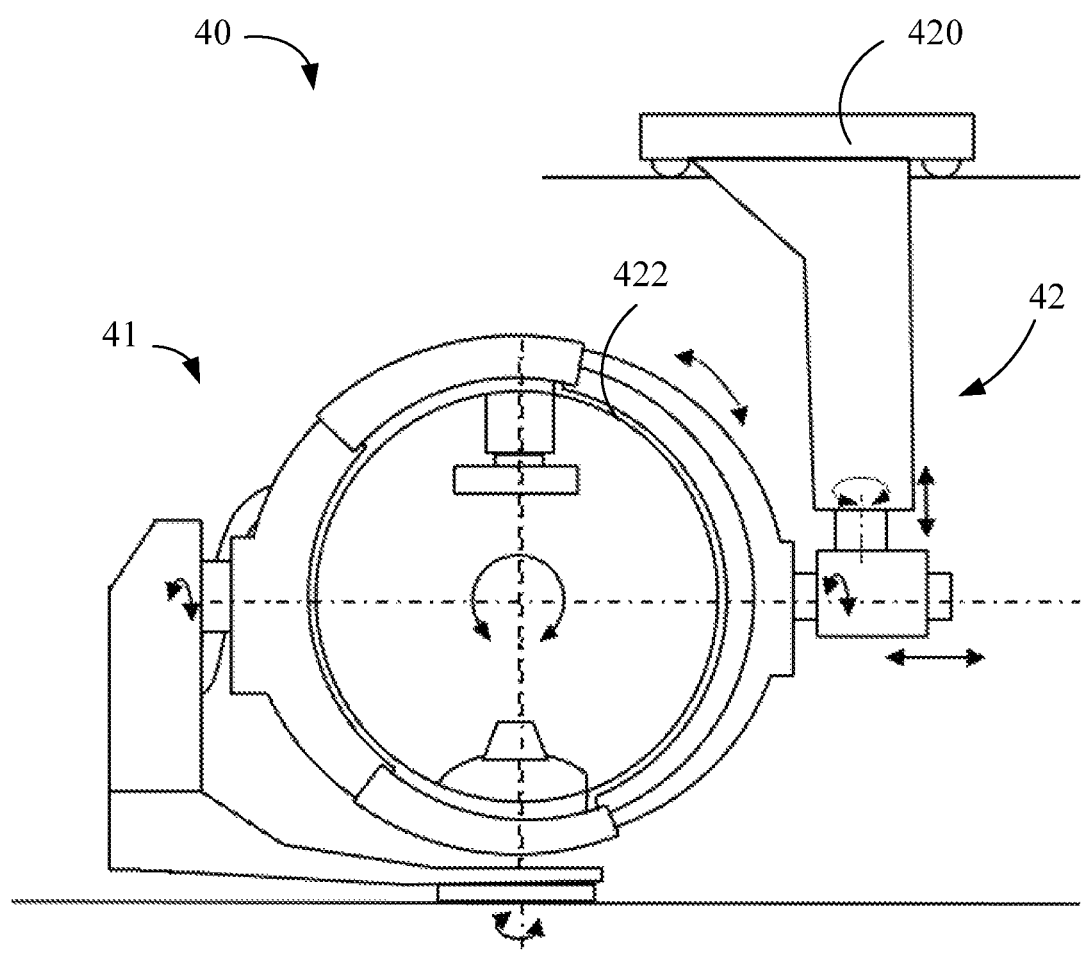
FIG. 6 is a schematic diagram illustrating an imaging system 40 according to an example of the present disclosure.

FIG. 6 is a schematic diagram illustrating an imaging system 40 according to another example of the present disclosure. The imaging system 40 shown in FIG. 6 mainly differs from the imaging system 10 shown in FIG. 1 in that: a second gantry 42 is a suspension gantry. A second bracket 420 of the second gantry 42 may be movably suspended on a ceiling to be combined with or separated from a first imaging device 41. The second bracket 420 may enable a second cantilever 422 slidably mounted on the second bracket to rotate about a transverse axis and a longitudinal axis, and may also drive the second cantilever 422 to ascend and descend.

In another example, the first gantry may be a movable gantry, and connection or separation between the first gantry and the second gantry may be realized by moving the first gantry. For example, the first gantry is movable and the second gantry is fixed, or the first gantry is movable and the second gantry is also movable. In another example, the first gantry and the second gantry may both be suspended gantries. For example, the suspended first gantry is fixed and the suspended second gantry is movable, or the suspended first gantry is movable and the suspended second gantry is fixed, or the suspended first gantry and the suspended second gantry are both movable. In another example, the first gantry may include a robotic arm supporting the first cantilever, and/or the second gantry may include a robotic arm supporting the second cantilever. The above are merely some examples, and the present disclosure is not limited to the above examples. The first gantry and the second gantry may be of other structures.

Figure 7:
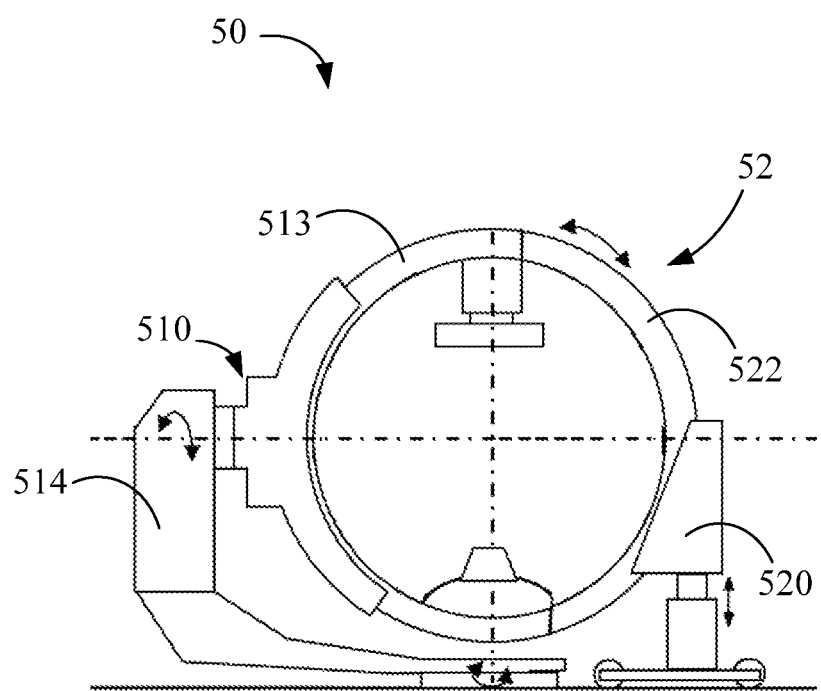
FIG. 7 is a schematic diagram illustrating an imaging system 50 according to an example of the present disclosure.
Figure 8:
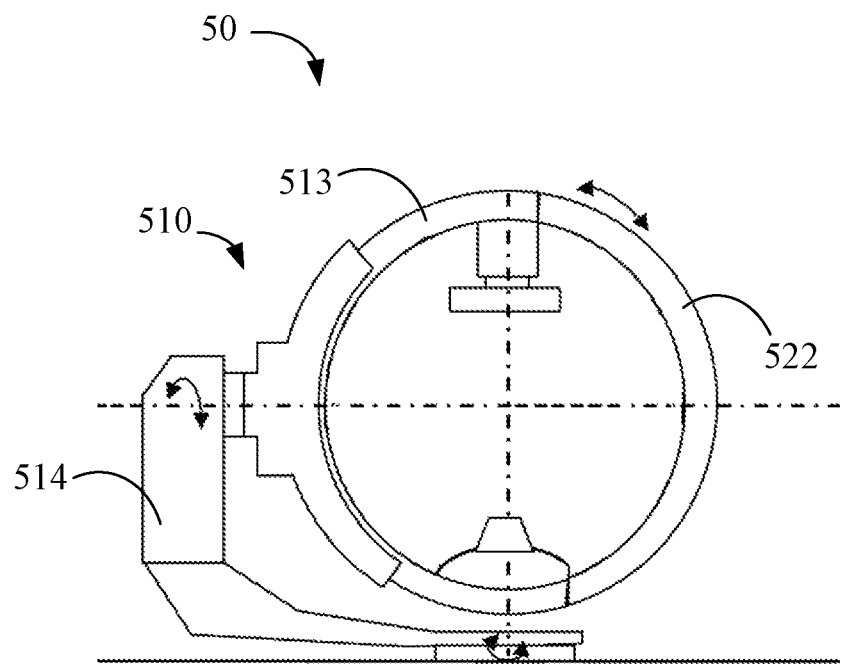
FIG. 8 is another schematic diagram illustrating the imaging system 50 shown in FIG. 7, where a second bracket and a scanning ring of the imaging system 50 are separated.

FIG. 7 is a schematic diagram illustrating an imaging system 50 according to another example of the present disclosure. The imaging system 50 shown in FIG. 7 mainly differs from the imaging system 10 shown in FIG. 1 in that: a second bracket 520 of a second gantry 52 configured to carry a second cantilever 522 is separable from the second cantilever 522. When the second cantilever 522 and a first cantilever 513 are connected and locked together, a first bracket 514 of a first gantry 510 carries a scanning ring formed by the first cantilever 513 and the second cantilever 522, and the second bracket 520 may be separated from the scanning ring. As shown in FIG. 8, the second bracket 520 may be moved away, and the first bracket 514 supports the first cantilever 513 and the second cantilever 522. Thus, the first bracket 514 has a strong carrying capacity.

FIGS. 5-8 all illustrate a state in which the first imaging device and the second gantry are connected and combined together. However, similar to the example shown in FIG. 1, the first imaging device of FIG. 5 to FIG. 8 may also be separated from the second gantry and operate as an independent imaging device. In addition, in some examples, similar to the examples of FIG. 3 and FIG. 4, the second gantry of FIG. 5 to FIG. 8 may also be assembled with the second X-ray source and the second detector into an independent third imaging device.

Figure 9:
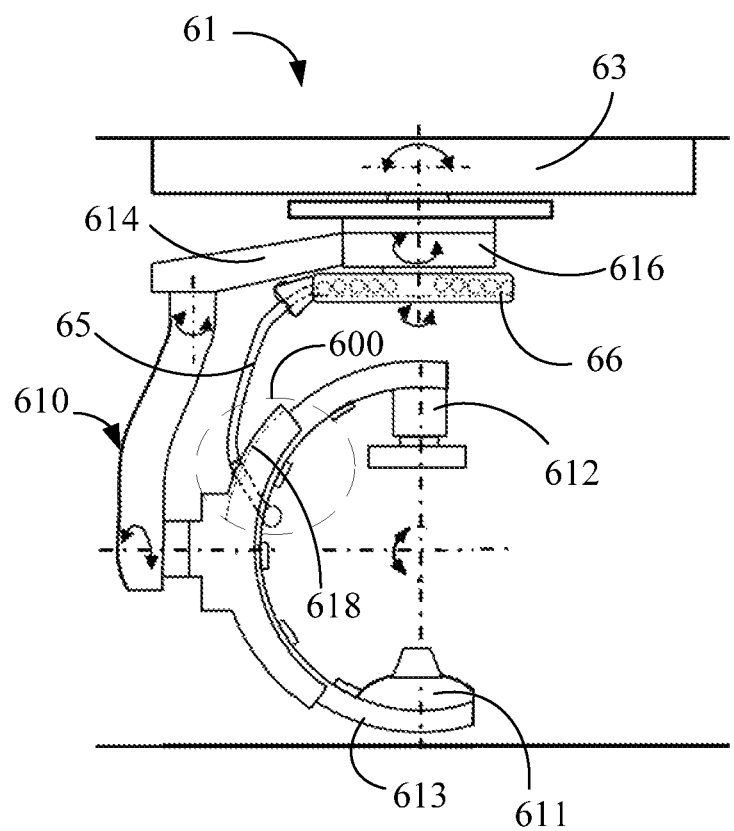
FIG. 9 is a schematic diagram illustrating a first imaging device 61 according to an example of the present disclosure.

FIG. 9 is a schematic diagram illustrating a first imaging device 61 according to another example of the present disclosure. The first imaging device 61 includes a cable 65 and a cable reel 66, where the cable reel 66 may receive the cable 65 and may reel the cable 65 in/out as a first cantilever 613 moves. One end of the cable 65 extends into the first cantilever 613 to electrically connect with a first X-ray source 611 and a first detector 612, and the other end extends out from the cable reel 66 to connect with a bus. A redundant part of the cable 65 is wound on the cable reel 66 to prevent excessive cable 65 from hanging outside and affecting movement of a first gantry 610. The cable 65 may protrude out from the cable reel 66 and extend outside the first gantry 610 with only part of the cable 65 extending into the first cantilever 613, thereby facilitating cable replacement and maintenance. Electricity may be transmitted to the first X-ray source 611 via the cable 65 and a control signal generated in a computer may be transmitted to the first X-ray source 611 and the first detector 612 via the cable 65, and a signal detected by the first detector 612 may also be transmitted to the computer via the cable 65.

In an example, the cable reel 66 may be rotatably provided on a first bracket 614. In an illustrated example, a first gantry 610 of the first imaging device 61 may be a suspended gantry. The cable reel 66 may rotate relative to the first bracket 614, or rotate together with the first bracket 614. A guide rail 63 may be mounted on a ceiling, the first bracket 614 includes a rotary table 616 mounted on the guide rail 63, and the rotary table 616 may horizontally rotate relative to the ceiling. The cable reel 66 may be mounted below the rotary table 616 and may rotate along with the rotary table 616, or may rotate relative to the rotary table 616.

Figure 10:
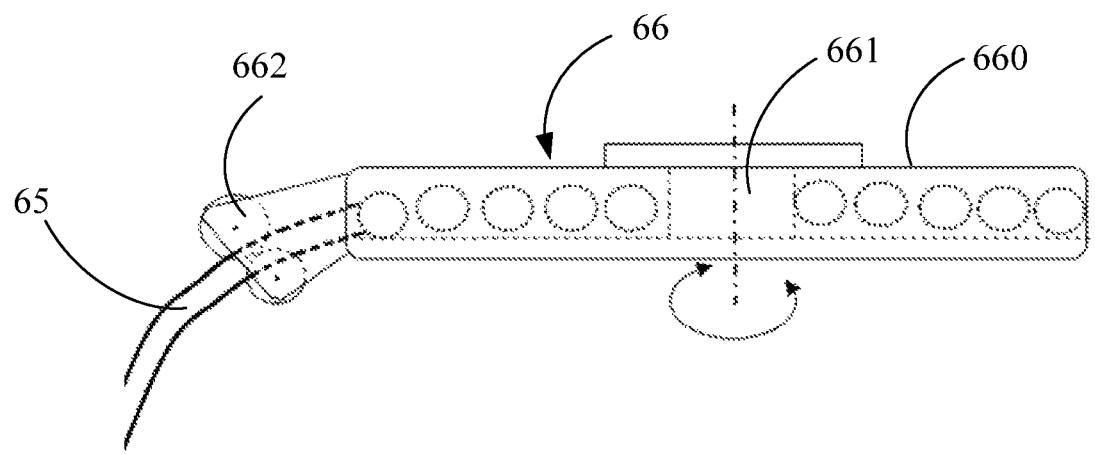
FIG. 10 is an enlarged view illustrating a cable reel of the first imaging device 61.
Figure 11:
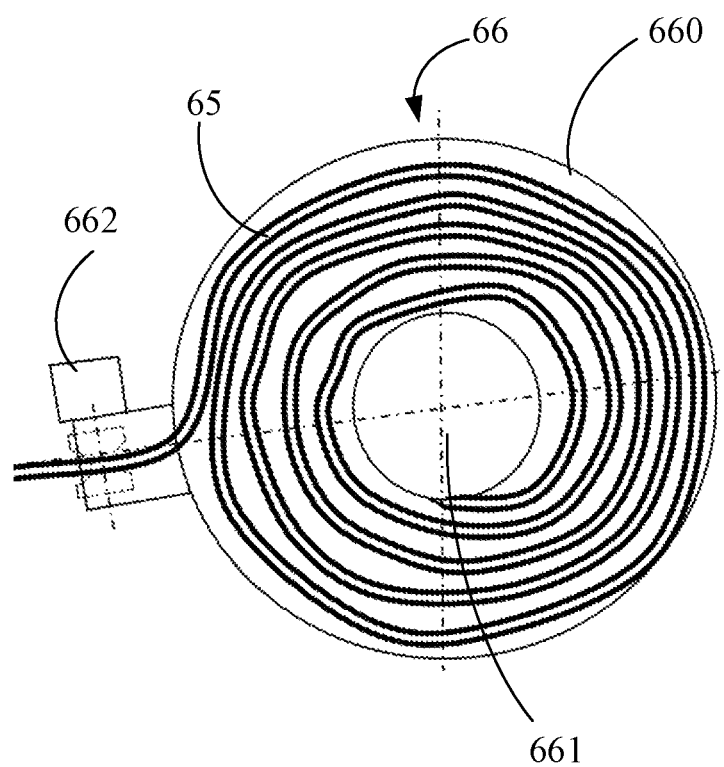
FIG. 11 is a top view illustrating the cable reel of the first imaging device 61.

FIG. 10 is an enlarged view illustrating the cable reel 66 shown in FIG. 9. FIG. 11 is a top view illustrating the cable reel 66 shown in FIG. 9. As shown in FIGS. 9-11, the cable reel 66 includes a receiving body 660 for receiving the cable 65 and a cable driving component 662 provided outside the receiving body 660. In the illustrated example, the receiving body 660 is disk-shaped. The receiving body 660 may include an inner shaft driving component 661 for driving the cable reel 66 to rotate about an inner shaft. The inner shaft driving component 661 may rotate clockwise or counter-clockwise to drive the receiving body 660 to rotate clockwise or counter-clockwise, so that the cable 65 may be reeled in or out. The inner shaft driving component 661 may include a motor, and the inner shaft of the cable reel 66 is a shaft of the motor.

When the first gantry 610 is stationary, the cable 65 is always subjected to an inward taking-up force. In an example, when the first gantry 610 is stationary, the inner shaft driving component 661 provides a particular torque to keep the cable 65 subjected to an inward taking-up force. In another example, the receiving body 660 is loaded by a spring, that is, the movement of the cable 65 away from the receiving body 660 causes the spring to be stretched, so that the cable 65 is always subjected to a taking-up force due to the stretching. For example, a spiral spring may be concentrically arranged on the inner shaft, or the spring may be arranged at an appropriate position of the receiving body 660, so that the cable 65 is subjected to a taking-up force.

The cable driving component 662 may be used to drive the cable 65 to be reeled in/out. In an example, the cable driving component 662 may be provided at a cable outlet of the receiving body 660. The cable 65 may extend out from the receiving body 660 and pass through the cable driving component 662, and further extend to the first gantry 610.

Figure 12:
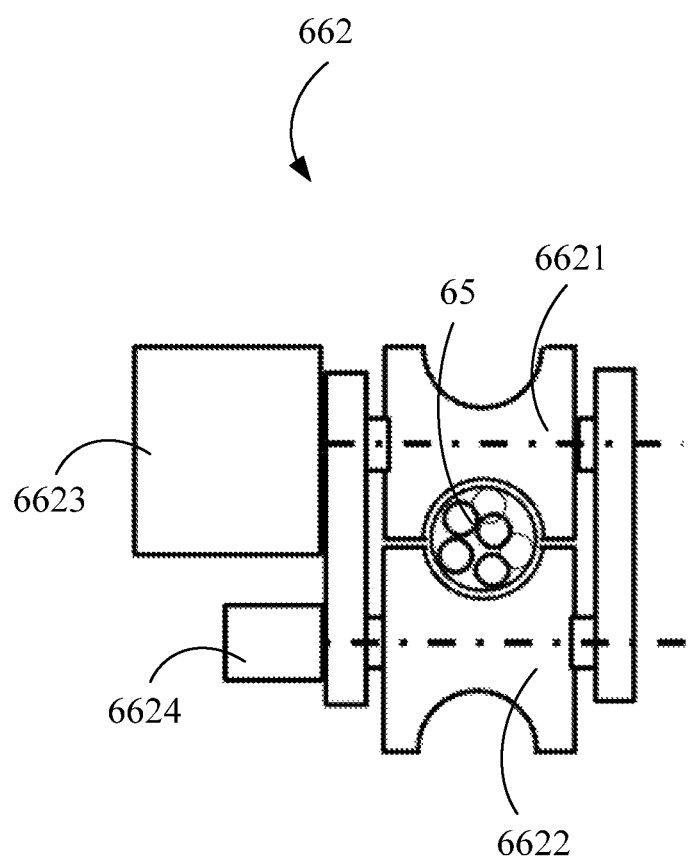
FIG. 12 is a schematic diagram illustrating a cable driving component of a cable reel.

FIG. 12 is a schematic diagram illustrating the cable driving component 662 at another angle. As shown in FIG. 12, the cable driving component 662 may include a driving wheel 6621, a driven wheel 6622, a motor 6623 and a sensor 6624. The cable 65 may pass through between the driving wheel 6621 and the driven wheel 6622. The motor 6623 may drive the driving wheel 6621 to rotate, thereby driving the driven wheel 6622 to rotate, so that the cable 65 may be reeled in to/out of the receiving body 660.

The sensor 6624 may be used to detect a moving tendency of the cable 65, i.e., a moving tendency of the cable being reeled in/out. The cable reel 66 may drive the cable 65 to move out of or into the receiving body 660 according to a signal of the sensor 6624. In an example, the sensor 6624 may be provided on the driven wheel 6622 for detecting a moving tendency of the driven wheel 6622 and sensing a moving tendency of the cable 65. In an example, the sensor 6624 includes a continuously rotating angle sensor or torque sensor. During a movement of the first gantry 610, when the cable protrudes with an insufficient length out of the cable reel 66, the driven wheel 6622 is acted upon by a frictional force of the cable 65. After the sensor 6624 senses the moving tendency of the cable 65, a control device (not shown) controls the motor 6623 to drive the driving wheel 6621 to move according to a signal of the sensor 6624, and the inner shaft driving component 661 rotates to release the cable 65 out of the cable reel 66. However, when the cable 65 protrudes out with an excessive length, the sensor 6624 detects an opposite moving tendency of the driven wheel 6622, the control device controls the motor 6623 to drive the driving wheel 6621 to move in an opposite direction according to a signal of the sensor 6624, and the inner shaft driving component 661 rotates in an opposite direction to reel the cable 65 in to the cable reel 66. In this case, the cable 65 may be reeled in/out automatically in such a way that the protruding cable 65 is sufficiently long and may be straighten up as possible, thereby preventing the cable 65 extending out with an excessive length. Thus, an impact of the cable 65 on the movement of the gantry is effectively reduced. In addition, due to driving action of the cable driving component 662, a pulling force of the cable 65 on the receiving body 660 may be effectively reduced, and a speed of reeling the cable 65 in/out may also be increased, thereby increasing a moving speed of the gantry.

Figure 13:
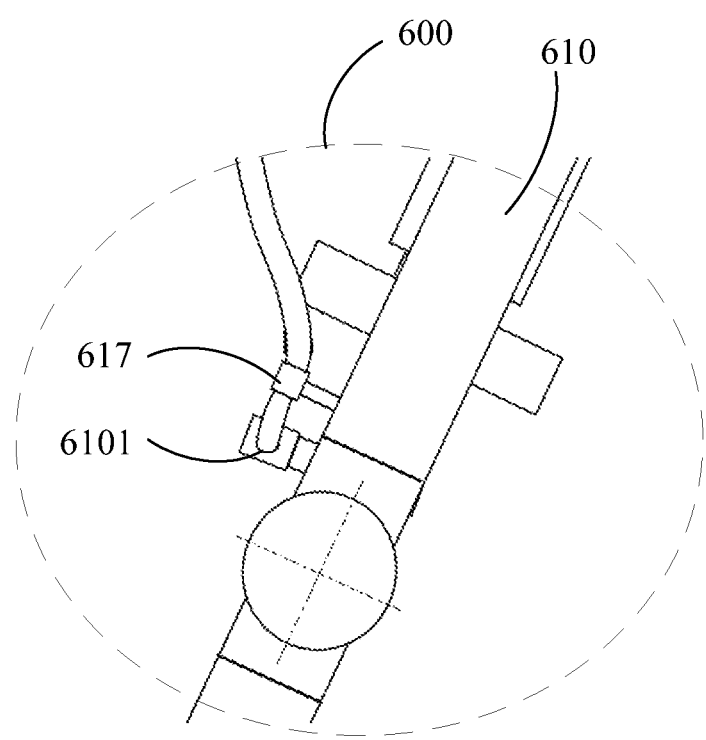
FIG. 13 is a partial enlarged view illustrating the first imaging device 61.

FIG. 13 is a schematic diagram illustrating an interior of a local region 600 of the first gantry 610 shown in FIG. 9. As shown in FIG. 9 and FIG. 13, the first imaging device 61 includes a cable sleeve 617 slidably provided on the first gantry 610, where the cable 65 may pass through the cable sleeve 617 and move in the cable sleeve 617. In an illustrated example, the first bracket 614 is provided with a sliding groove 618. The cable sleeve 617 may be slidably provided in the sliding groove 618, and may slide in the sliding groove 618 along with the movement of the cable 65, and automatically adjust a position, thereby preventing a bending angle of the cable 65 at a cable inlet 6101 of the first gantry 610 being too large. In an example, a vertical distance from the top of the cable sleeve 617 to the first gantry 610 is constant, that is, the distance from the top of the cable sleeve 617 to the sliding groove 618 is constant. In this way, the cable 65 is always pulled close to the first gantry 610.

Figure 14:
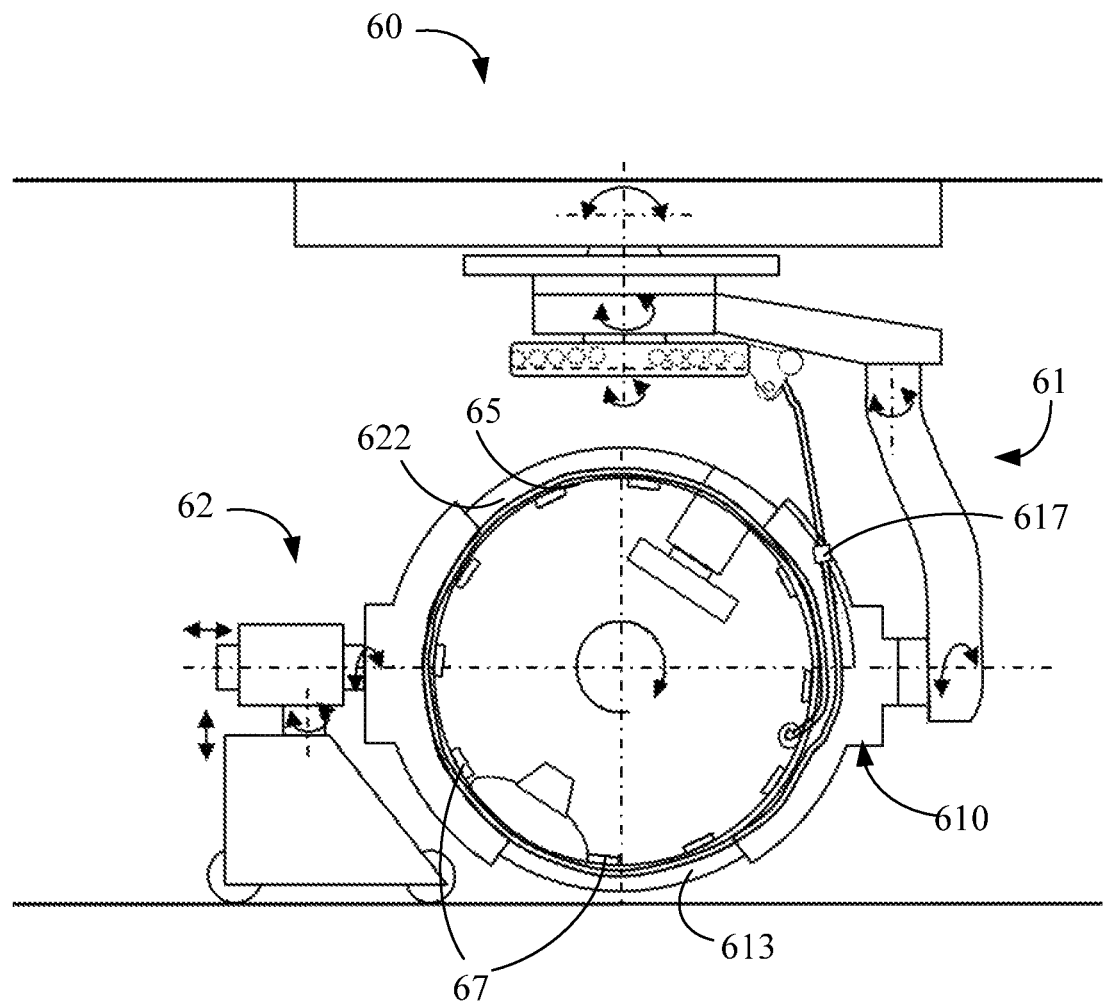
FIG. 14 is a schematic diagram illustrating an imaging system 60 according to an example of the present disclosure, where the imaging system 60 includes the first imaging device 61 shown in FIG. 9.

FIG. 14 is a schematic diagram illustrating an imaging system 60 according to another example of the present disclosure, where the imaging system 60 includes the first imaging device 61 shown in FIG. 9. FIG. 14 illustrates a state in which the first imaging device 61 and a second gantry 62 are connected and combined together. In the illustrated example, the imaging system 60 includes a plurality of cable supports 67 provided at an inner side of the first cantilever 613 and an inner side of a second cantilever 622, where the cable supports 67 are used to support the cable 65 so that the cable 65 may extend along inner sides of the first cantilever 613 and the second cantilever 622. When a scanning ring formed by the first cantilever 613 and the second cantilever 622 rotates, the cable 65 is supported by the cable supports 67 and extends along the inner sides of the first cantilever 613 and the second cantilever 622. The cable sleeve 617 may pull the cable 65 close to the first bracket 614, so that the cable 65 is close to the inner sides of the first cantilever 613 and the second cantilever 622 and placed on the cable supports 67 when the scanning ring rotates. The cable 65 may run one or more circles along the inner side of the scanning ring.

Figure 15:
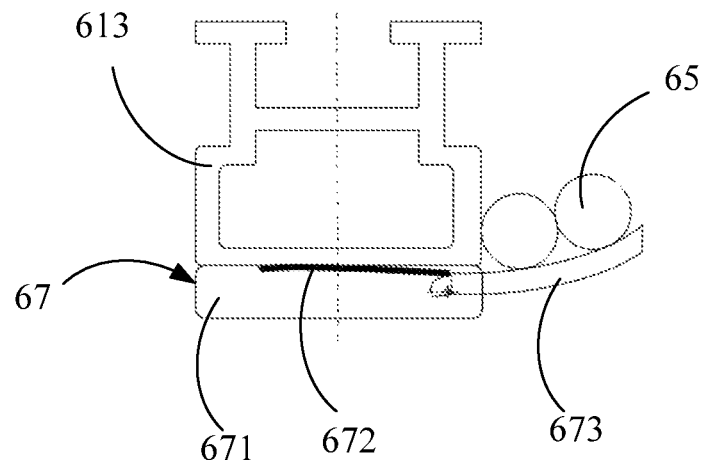
FIG. 15 is a schematic diagram illustrating a cable support of the imaging system 60 according to an example of the present disclosure, where a supporting element of the cable support protrudes out.
Figure 16:
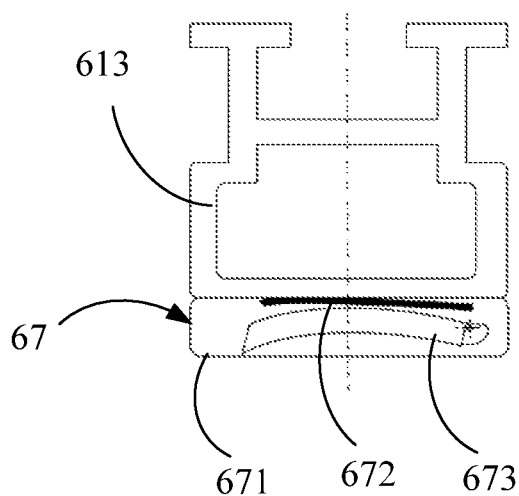
FIG. 16 is a schematic diagram illustrating another state of the cable support of the imaging system 60, where the supporting element of the cable support is folded back.

FIG. 15 is a side view illustrating the cable support 67 supporting a cable. FIG. 16 is a side view illustrating a fold-back state of the cable support 67. Description will be made below with the cable support 67 provided on the first cantilever 613 as an example. The cable support 67 includes a supporting element 673 capable of protruding from the inner side of the first cantilever 613 or folding back to the inner side of the first cantilever 613. When protruding from the inner side of the first cantilever 613, the supporting element 673 may support the cable 65. The supporting element 673 may fold back to the inner side of the first cantilever 613 when the supporting element is not used.

In the illustrated example, the cable support 67 also includes a body 671 and an elastic element 672. The body 671 is mounted at the inner side of the first cantilever 613. The elastic element 672 is received in the body 671, and the elastic element 672 may include a spring sheet. One end of the supporting element 673 is rotatably connected to the body 671. The supporting element 673 may rotate to protrude out from the body 671, and be located outside the first cantilever 613. The elastic element 672 may provide a pushing force for assisting in pushing the supporting element 673 to rotate out. In the illustrated example, the supporting element 673 is of an arc shape. When protruding from the body 671, the supporting element 673 bends toward the inner side of the first cantilever 613 to bring the cable 65 close to the inner side of the first cantilever 613. The supporting element 673 may also rotatably fold back to inside of the body 671 when the supporting element 673 is not used, as shown in FIG. 16. The cable support 67 provided on the second cantilever 622 has a same structure as the cable support 67 provided on the first cantilever 613, which will not be described herein.

The cable reel 66, the cable sleeve 617 and/or the cable support 67 shown in FIGS. 9 to 16 may be used not only in the example of the suspended gantry shown in FIG. 9, but also in the example of the floor type gantry. For example, the cable reel 16 shown in FIG. 1 has a structure and an operating manner similar to those of the cable reel 66. The cable reel 16 in FIG. 1 is mounted on a ceiling, and the cable 15 hangs from the ceiling. In some examples, the cable reel 66, the cable sleeve 617 and/or the cable support 67 may be applied not only to an angiography machine, but also to a CBCT apparatus, or another scanning apparatus with a large rotating angle.

Figure 17:
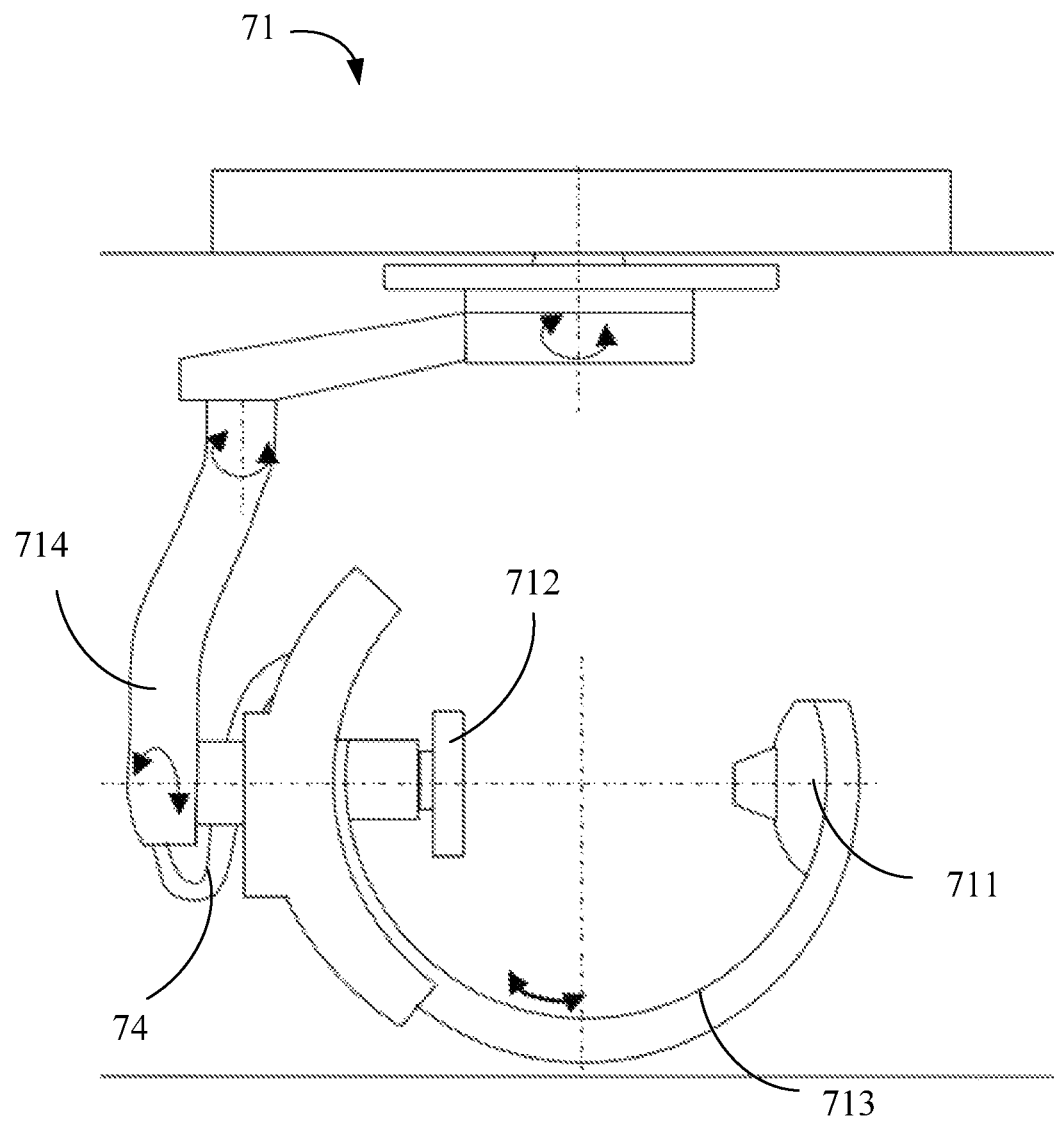
FIG. 17 is a schematic diagram illustrating a first imaging device 71 according to an example of the present disclosure.
Figure 18:
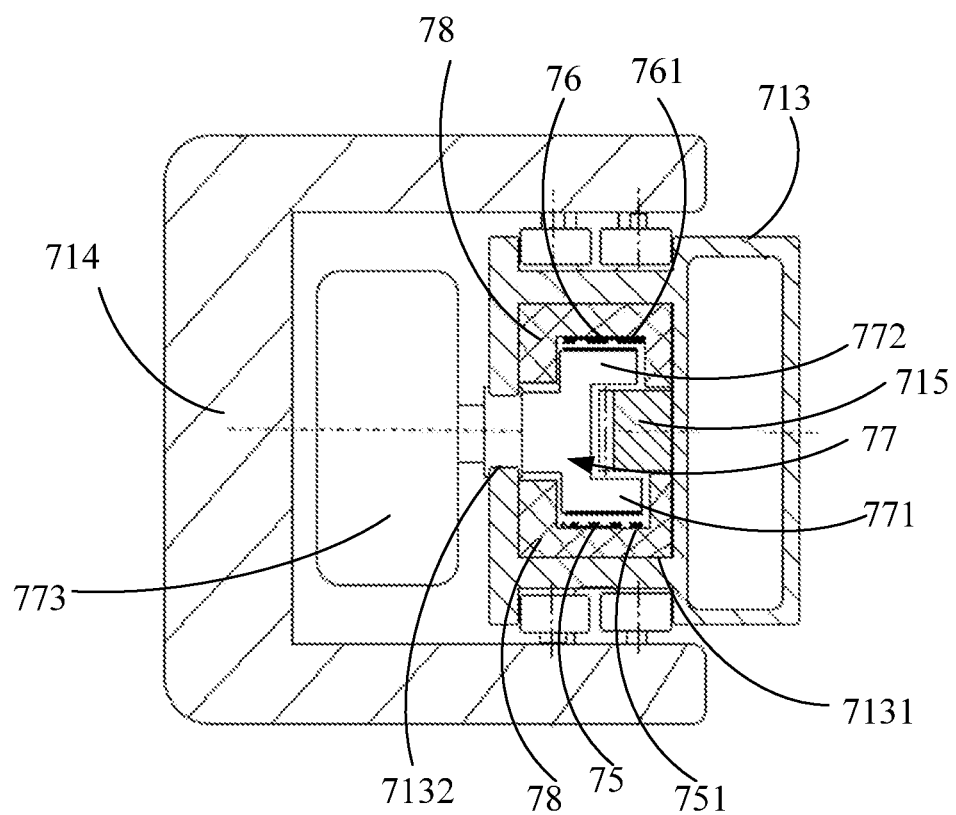
FIG. 18 is a transverse sectional view illustrating a connection of a first cantilever and a first bracket of the first imaging device 71.
Figure 19:
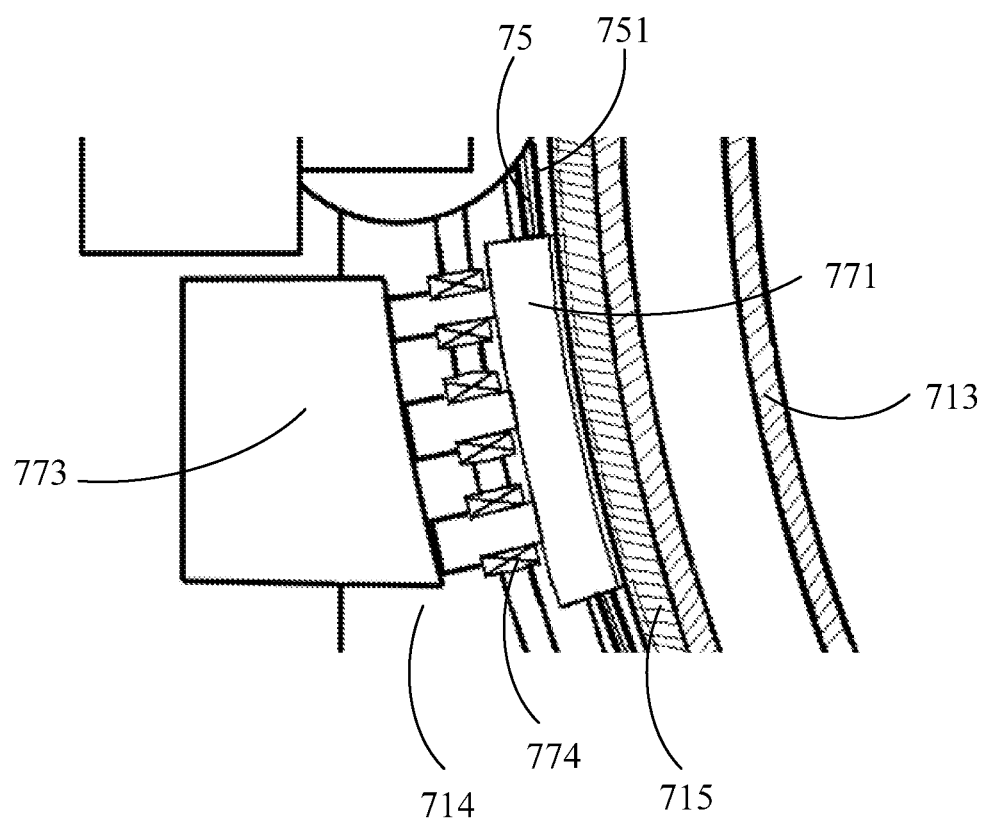
FIG. 19 is a partial longitudinal sectional view illustrating the connection of the first cantilever and the first bracket of the first imaging device 71.

FIG. 17 is a schematic diagram illustrating a first imaging device 71 according to another example of the present disclosure. FIG. 18 is a cross sectional view illustrating a connection of a first bracket 714 and a first cantilever 713 of the first imaging device 71 shown in FIG. 17. FIG. 19 is a side sectional view illustrating a connection of the first bracket 714 and the first cantilever 713. The first imaging device 71 may include sliding strips 75 and 76 and a sliding contact piece 77. The sliding strips 75 and 76 are provided at an outer side of the first cantilever 713, i.e., one side on which the first cantilever 713 and the first bracket 714 are slidably connected, and the sliding strips 75 and 76 may extend along the first cantilever 713 and be electrically connected with a first X-ray source 711 and a first detector 712.

In this example, an outer side of the first cantilever 713 may be provided with a groove 7131 extending along the first cantilever 713, and the sliding strips 75 and 76 are provided in the groove 7131. The groove 7131 has an opening 7132 extending along the first cantilever 713, and the opening 7132 is provided on an outer side surface of the first cantilever 713. In the illustrated example, the sliding strips may include a first sliding strip 75 and a second sliding strip 76. The first sliding strip 75 and the second sliding strip 76 are separately arranged. The first sliding strip 75 is close to a front side wall of the first cantilever 713 and extends in the groove 7131, and the second sliding strip 76 is close to a back side wall of the first cantilever 713 and extends in the groove 7131. In an example, the first sliding strip 75 may be used to transmit low-voltage electricity and signals, and the second sliding strip 76 may be used to transmit high-voltage electricity. The first sliding strip 75 may include a plurality of first sliding rails 751. Four sliding rails shown herein may be connected to positive and negative poles of the low-voltage electricity and positive and negative ends of the signals respectively. The second sliding strip 76 may include a plurality of second sliding rails 761. Three sliding rails shown herein may be connected to a positive pole, a negative pole and a grounding end of the high-voltage electricity, respectively.

The sliding contact piece 77 is fixed to the first bracket 714, and may be in slidable electrical contact with the sliding strips 75 and 76. When the first cantilever 713 slides relative to the first bracket 714, the sliding strips 75 and 76 slide relative to the sliding contact piece 77 and may always keep in an electrical connection with the sliding contact piece 77. The sliding contract piece 77 is electrically connected with a cable 74 outside the first cantilever 713 and further connected to a bus, thereby realizing transmission of electricity and signals. A sliding connection between the sliding contact piece 77 and the sliding strips may cause less interference to movements of cantilevers and brackets, so that the cantilevers may move more freely, and the moving speed of the cantilevers may be effectively improved, thereby bringing less interference to a doctor and a subject. In addition, compared to a traditional thick cable, with the sliding strips of the present disclosure, a problem that reliability of electrical connection is reduced due to long-term repeated bending of a thick cable may be effectively avoided, improving the reliability of electrical connection of the sliding strips and the sliding contact piece.

In the illustrated example, the sliding contact piece 77 may protrude into the groove 7131 to electrically connect with the sliding strips 75 and 76. The sliding contact piece 77 is located between the first sliding strip 75 and the second sliding strip 76. In an example, the sliding contact piece 77 may include an electric brush.

The sliding contact piece 77 may include contact heads 771 and 772, a support 773 and a support wheel 774. The contact head 771 and the contact head 772 are separately arranged with a particular spacing, and are in electrical contact with the first sliding strip 75 and the second sliding strip 76, respectively. In this way, the first sliding strip 75 for transmitting low-voltage electricity and signals and the second sliding strip 76 for transmitting high-voltage electricity are spaced at a large distance, which may effectively avoid interference. An insulator 78 may be provided between the sliding strips 75 and 76 and the first cantilever 713 to provide electrical insulation, thereby effectively avoiding an electric leakage and interference. The insulator 78 may extend along the first cantilever 713 and surround an electrical contact position between the sliding strips 75 and 76 and the sliding contact piece 77 to isolate the electrical contact position from the outside.

The support 773 may be fixed to the first bracket 714. The support 773 may be provided outside the groove 7131. The support wheel 774 may be rollably provided between the support 773 and the contact heads 771 and 772. The support wheel 774 may be used to adjust the position of the sliding contact piece 77, so that the contact heads 771 and 772 may be in better electrical contact with the sliding strips 75 and 76 in a sliding process.

Figure 20:
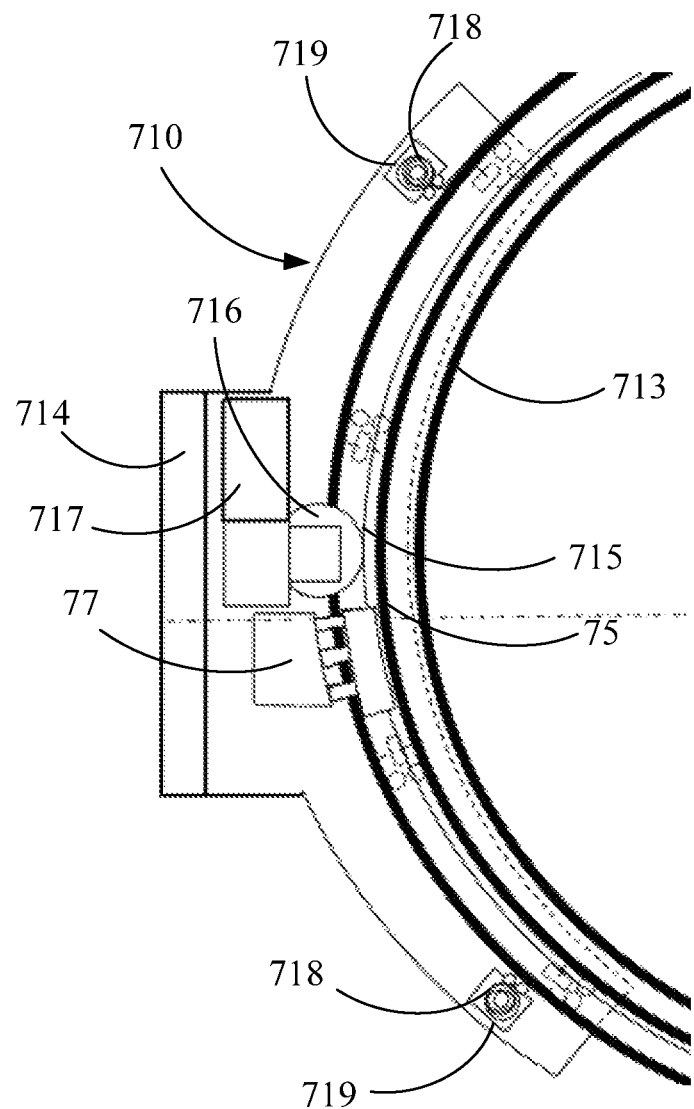
FIG. 20 is a partial schematic diagram illustrating the first imaging device 71.

FIG. 20 is a partial schematic diagram illustrating a first gantry 710 and a first cantilever 713. As shown FIG. 18 and FIG. 19, in this example, the first imaging device 71 may include a rack 715 provided at an outer side of the first cantilever 713 and a driving gear 716 engaged with the rack 715. The rack 715 extends along the first cantilever 713. The first imaging device 71 may also include a driving motor 717, and the driving motor 717 drives the driving gear 716 to drive the rack 715 to move. The rack 715 is arc-shaped, and is provided in the groove 7131. In an example, the insulator 78 may also be provided between the rack 715 and the sliding strips 75 and 76 to provide effective insulation.

Figure 21:
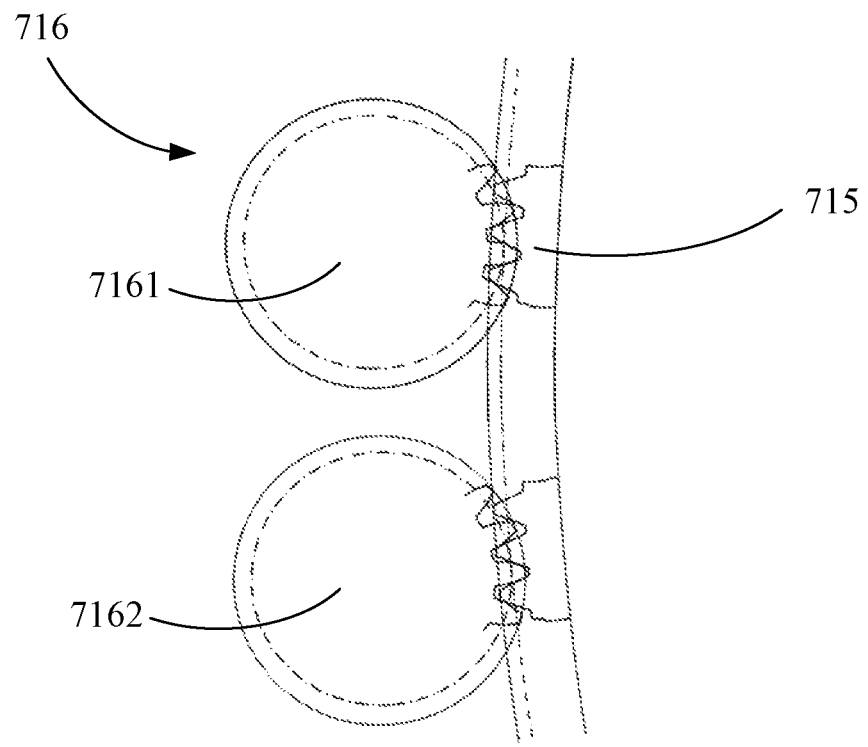
FIG. 21 is a schematic diagram illustrating an engagement of a rack and a driving gear of the first imaging device 71.

FIG. 21 is a schematic diagram illustrating an engagement of the rack 715 and the driving gear 716. In the illustrated example, the driving gear 716 may include a first driving gear 7161 and a second driving gear 7162, both of which are engaged with the rack 715. The first driving gear 7161 and the second driving gear 7162 may be driven by a corresponding driving motor, respectively. With a double-gear driving manner, a gap between the gears may be eliminated and moving speeds may be effectively increased. In another example, a single gear and a single motor may be used for driving.

Figure 22:
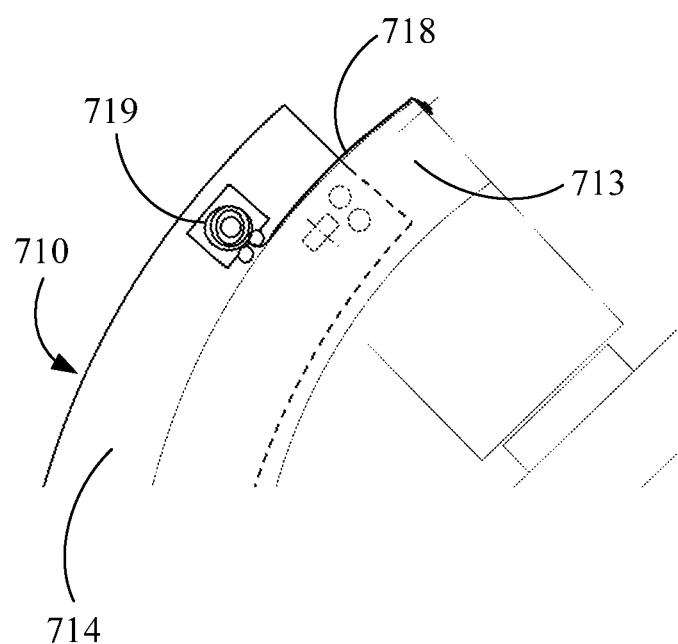
FIG. 22 is a schematic diagram illustrating a sealing strip take-up device of the first imaging device 71.
Figure 23:
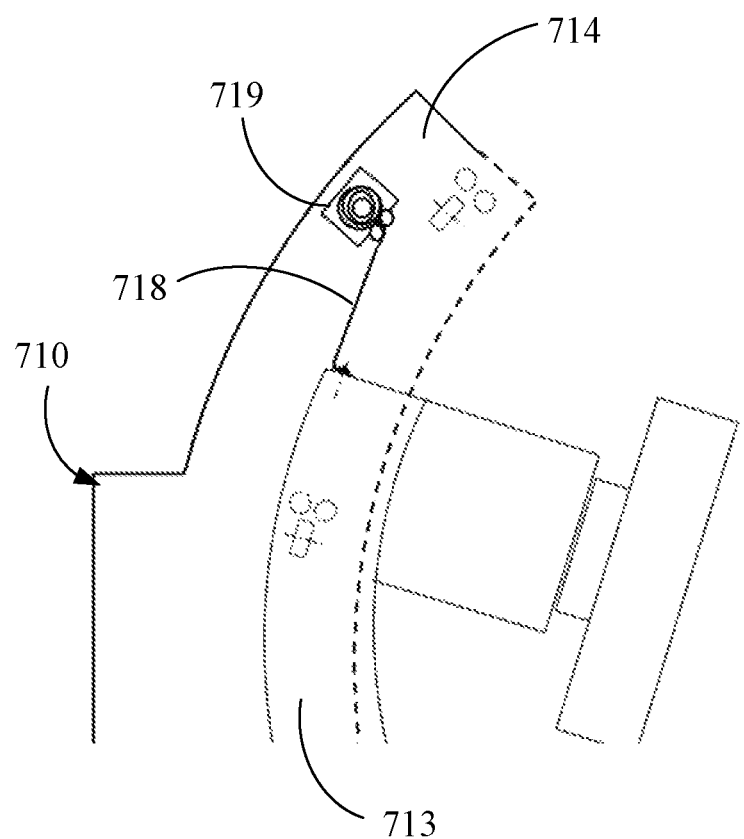
FIG. 23 is a schematic diagram illustrating another state of the sealing strip take-up device shown in FIG. 22.

FIG. 22 and FIG. 23 are schematic diagrams illustrating different states of a sealing strip reel 719, respectively. As shown in FIG. 20, in this example, the first imaging device 71 may include a sealing strip 718 and a sealing strip reel 719. One end of the sealing strip 718 is fixedly connected with the first cantilever 713. In the illustrated example, one end of the sealing strip 718 may be fixed to one end surface of the first cantilever 713 and the other end of the sealing strip 718 is fixed to the sealing strip reel 719 which is provided on the first bracket 714. The sealing strip reel 719 may reel the sealing strip 718 in/out as the first cantilever 713 slides, so that an opening 7132 (as shown in FIG. 18) that is on the groove 7131 and exposed outside the first bracket 714 may be sealed up by the sealing strip 718. In the illustrated example, both ends of the first bracket 714 may be mounted with the sealing strip reel 719, respectively.

When one end of the first cantilever 713 slides out of the first bracket 714, as shown in FIG. 22, the opening 7132 of the groove 7131 is exposed, and the sealing strip 718 in the sealing strip reel 719 is pulled out to seal the exposed opening 7132, thereby effectively preventing dusts or debris from entering the groove 7131 and improving safety. When one end of the first cantilever 713 slides into the first bracket 714, as shown in FIG. 23, the sealing strip 718 may not seal the opening 7132 and may be pulled out as the first cantilever 713 slides.

The first imaging device 71 shown in FIGS. 17 to 23 may be applied to the above imaging system, and may be combined with the second gantry to form a second imaging device. The second gantry may be provided with the above sliding strips at an outer side of the second cantilever thereof. After the second gantry is connected with the first imaging device, the second cantilever is connected with the first cantilever 713 to form a scanning ring of full rotation, and the sliding strips of the second cantilever are connected with the sliding strips 75 and 76 of the first cantilever 713 to form a complete sliding ring, that is, the sliding strips are provided at an outer side of the scanning ring and extend along the scanning ring. In an example, a groove extending along the second cantilever is opened on an outer side of the second cantilever and may be connected with the groove of the first cantilever to form a complete circle of groove, that is, a groove extending along the scanning ring is opened on an outer side of the scanning ring. In an example, an insulator may be provided between the second cantilever and the sliding strips. After the second gantry is combined with the first imaging device, the insulator on the second cantilever is connected with the insulator 78 on the first cantilever, and the insulators may be provided between the sliding strips and the scanning ring and extend along the scanning ring.

In an example, the sliding contact piece 77 of the first imaging device 71 may be slidably and electrically connected with the sliding strips 75 and 76 on the first cantilever 713 and the sliding strips on the second cantilever. This sliding connection between the sliding contact piece and the sliding strips may facilitate the second imaging device to rotate one or more circles. For example, in a CBCT scan, a full-rotation movement of the scanning ring may be facilitated. In another example, another sliding contact piece may be provided on the second gantry. When the second gantry is combined with the second X-ray source and the second detector to form the third imaging device, the sliding contact piece may be electrically connected with the sliding strip on the second cantilever for transmitting electricity and signals.

In some examples, a rack may be provided on the second cantilever of the second gantry, and the rack provided on the second cantilever may be connected with the rack 715 on the first cantilever 713 to form a complete circle of rack, that is, the rack is provided at an outer side of the scanning ring and extends along the scanning ring. In some examples, the second gantry may be provided with the sealing strip 718 and a sealing strip reel 719 as above for sealing an opening that is on the groove of the second cantilever and exposed outside. In some examples, some other components of the first imaging device 71 may also be provided on the second gantry, and the second gantry may be combined with the first imaging device 71 to perform one or more circles of rotation. The second cantilever may have a structure similar to that of the first cantilever 713.

The above descriptions are merely some examples and are not limited to the above examples. The sliding strips 75 and 76, the sliding contact piece 77, the rack 715, the sealing strip 718, the sealing strip reel 719 and/or other components of the first imaging device 71 may be used in another gantry, such as a floor-type gantry.

Figure 24:
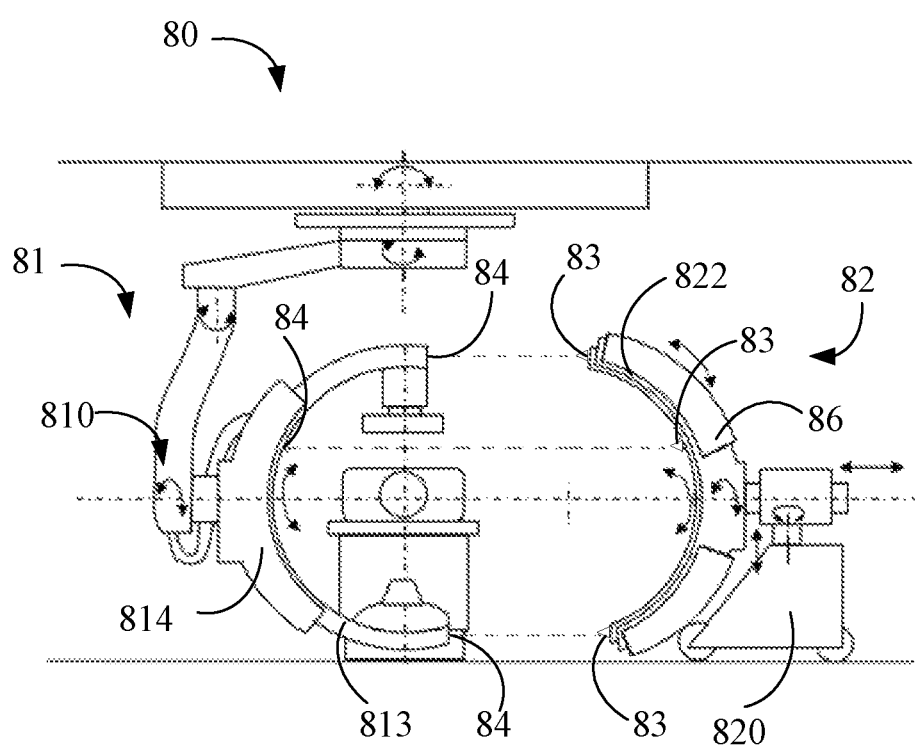
FIG. 24 is a schematic diagram illustrating an imaging system 80 according to an example of the present disclosure, where a first imaging device and a second gantry of the imaging system 80 are separated.

FIG. 24 is a schematic diagram illustrating an imaging system 80 according to another example of the present disclosure, where a first imaging device 81 is not combined with the second gantry 82. The imaging system 80 may include a laser emitter 83 provided on one of a first cantilever 813 and a second cantilever 822 for emitting laser. The other one of the first cantilever 813 and the second cantilever 822 is provided with a marking point 84 corresponding to the laser emitter 83. The laser may be emitted onto a corresponding marking point by moving a gantry for positioning. In an example, the laser emitter 83 may be provided on the second cantilever 822, and the first cantilever 813 may be provided with a corresponding marking point 84. The laser emitter 83 may be provided on both ends and/or a middle position of the second cantilever 822. The second gantry 82 is moved close to the first gantry 810, and a position of the second gantry 82 and/or a position of the second cantilever 822 are adjusted according to a position that is on the first gantry 810 and hit by laser emitted by the laser emitter 83 and a position of the marking point 84 to ensure the laser hits on the marking point 84. In this way, relative positions of the first cantilever 813 and the second cantilever 822 may be determined. In another example, the laser emitter 83 may be provided on the first cantilever 813 of the first gantry 810, and the second cantilever 822 is provided with the marking point 84 corresponding to the laser emitter 83. In still another example, the first cantilever 813 may be provided with one or more laser emitters 83, the second cantilever 822 may also be provided with one or more laser emitters 83, and corresponding marking points 84 are arranged respectively.

Figure 25:
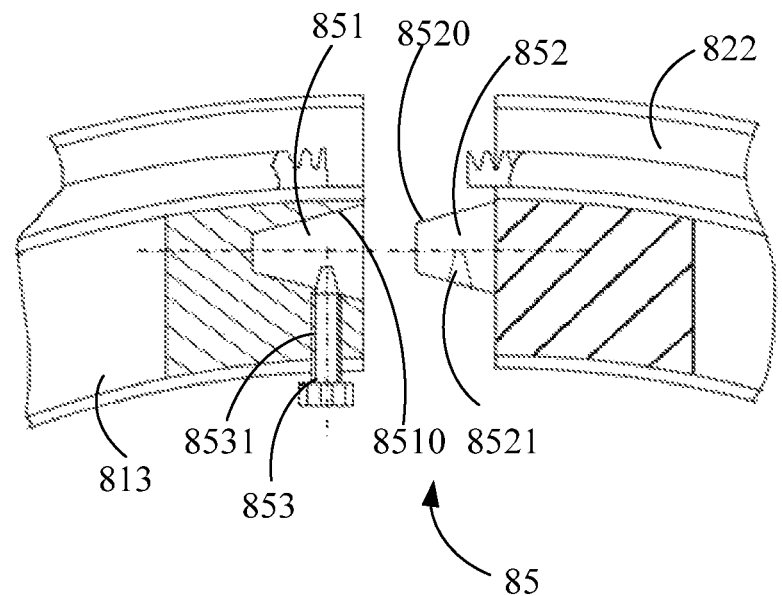
FIG. 25 is a schematic diagram illustrating an aligning and locking device of the imaging system 80 according to an example of the present disclosure.
Figure 26:
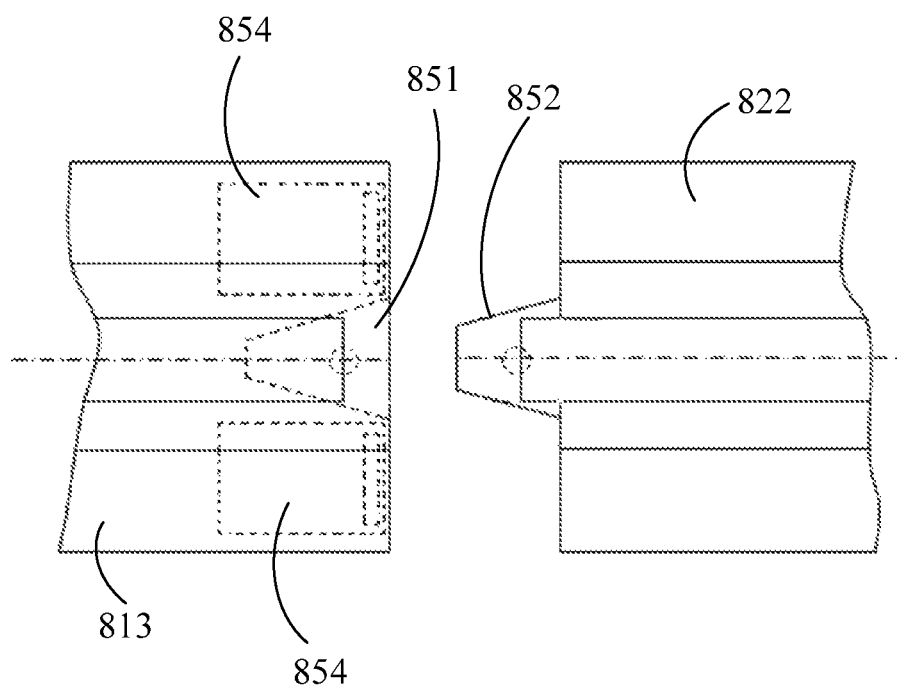
FIG. 26 is a top view illustrating the aligning and locking device shown in FIG. 25.
Figure 27:
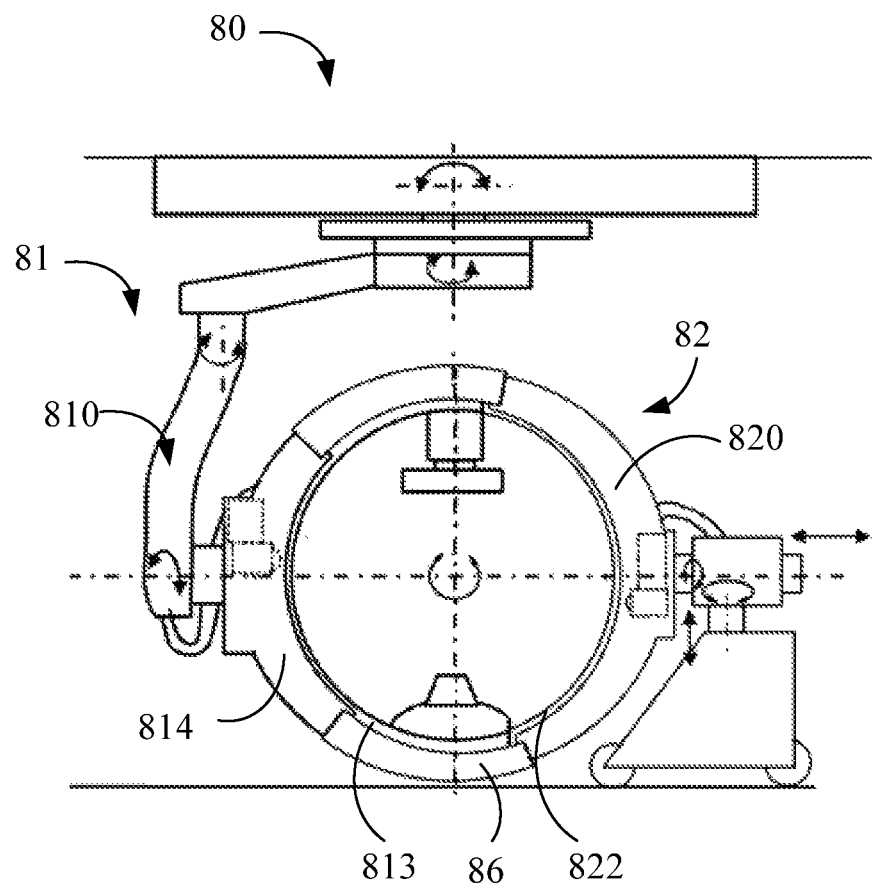
FIG. 27 is a schematic diagram illustrating another state of the imaging system 80, where the first imaging device and the second gantry are combined together by connection.

FIG. 25 is a schematic diagram illustrating part of the imaging system 80 shown in FIG. 24. FIG. 26 is a top view illustrating the imaging system 80 shown in FIG. 25. FIG. 27 is a schematic diagram illustrating another state of the imaging system 80 shown in FIG. 24, where the first imaging device 81 and the second gantry 82 are combined together. As shown in FIGS. 25 to 27, in this example, the imaging system 80 may include an aligning and locking device 85 provided at a connection of the first cantilever 813 and the second cantilever 822. In an example, both ends of the first cantilever 813 and the second cantilever 822 are provided with the aligning and locking device 85, respectively. The aligning and locking device 85 may include a positioning groove 851 and a positioning block 852. The positioning groove 851 is concavely provided on one of the first cantilever 813 and the second cantilever 822, the positioning block 852 is convexly provided on the other one of the first cantilever 813 and the second cantilever 822 and may extend into the positioning groove 851 to cooperate with the positioning groove 851 for positioning. In the illustrated example, the positioning groove 851 is concavely provided on an end of the first cantilever 813, and the positioning block 852 is convexly provided on an end of the second cantilever 822. In another example, the positioning groove 851 is concavely provided on an end of the second cantilever 822, and the positioning block 852 is convexly provided on an end of the first cantilever 813. In still another example, the positioning groove 851 of the aligning and locking device 85 provided on corresponding ends of the first cantilever 813 and the second cantilever 822 is concavely provided on one end of the first cantilever 813, and the positioning block 852 is convexly provided on one end of the second cantilever 822; while the positioning groove 851 of the aligning and locking apparatus 85 provided on the remaining ends of the first cantilever 813 and the second cantilever 822 is concavely provided on the other end of the second cantilever 822, and the positioning block 852 is convexly provided on the other end of the first cantilever 813.

The positioning groove 851 gradually becomes smaller from outside to inside, and the positioning block 852 is of a shape corresponding to the positioning groove 851. In the illustrated example, the positioning groove 851 is a cone-shaped groove, and the positioning block 852 is a cone-shaped body. In other examples, the positioning groove 851 and the positioning 852 may have another shape.

The positioning block 852 is concavely provided with a locking groove 8521. The aligning and locking device 85 includes a locking member 853 movably provided in the one of the first cantilever 813 and the second cantilever 822 where the positioning groove 851 is located and the locking member 853 may be inserted into the locking groove 8521 to cooperate with the locking groove 8521 for locking. In the illustrated example, the locking member 853 is movably provided in an inner side of the first cantilever 813. In an example, the locking member 853 may include a locking screw that has threads 8531 and is rotatably screwed in one of the first cantilever 813 and the second cantilever 822. Before the first cantilever 813 and the second cantilever 822 are connected, the locking screw 853 may be screwed in such a way that an end of the locking screw does not protrude into the positioning groove 851. After the first cantilever 813 and the second cantilever 822 are connected, the positioning block 852 is inserted into the positioning groove 851, and the locking screw 853 may be screwed into the locking groove 8521, thereby locking ends of the first cantilever 813 and the second cantilever 822. When the first cantilever 813 and the second cantilever 822 are separated, the locking screw 853 may be unscrewed out of the locking groove 8521.

In an example, an inner wall 8510 of the positioning groove 851 is a first guide wall of the first cantilever 813. An outer side wall 8520 of the positioning block 852 is a second guide wall that is on the second cantilever 822 and cooperates with the first guide wall 8510. The second guide wall 8520 is fitted to the first guide wall 8510 and guides connection of the first cantilever 813 and the second cantilever 822. The locking member 853 may be inserted through the first guide wall 8510 and the second guide wall 8520 to lock the first cantilever 813 and the second cantilever 822. In other examples, the first guide wall 8510 and the second guide wall 8520 may be another wall that extends obliquely and has a guiding function.

In an example, the aligning and locking device 85 may also include a first electromagnet 854 provided on one of the first cantilever 813 and the second cantilever 822, and the first electromagnet 854 generates a magnetic force to attract the other one of the first cantilever 813 and the second cantilever 822. In the illustrated example, the first electromagnet 854 may be mounted on the first cantilever 813. Also, the aligning and locking device 85 may also include two first electromagnets 854 mounted on both sides of the positioning groove 851, respectively. When the second gantry 82 is far from the first gantry 810, the second cantilever 822 may be moved close to the first cantilever 813 by laser positioning. When a distance between the second cantilever 822 and the first cantilever 813 is within a particular distance range, the first electromagnet 854 may be energized to generate a magnetic force to attract the second cantilever 822. Under guide of the positioning block 852, the first cantilever 813 and the second cantilever 822 may be aligned and made to be close to each other, and then, the locking member 853 may be inserted into the locking groove 8521. The distance range may be determined according to the magnetic force of the first electromagnet 854 to ensure that the first electromagnet 854 may attract the second cantilever 822 and the first cantilever 813 together within this distance range. In an example, the first electromagnet 854 may be energized to generate a magnetic force of 50 kgf or more.

The imaging system 80 may also include a lock cover 86 slidably provided outside the first cantilever 813 and the second cantilever 822 and configured to cover the first cantilever 813 and the second cantilever 822. When the first cantilever 813 and the second cantilever 822 are separated, the lock cover 86 may cover one of the first cantilever 813 and the second cantilever 822. For example, the lock cover 86 shown herein covers the second cantilever 822, and the lock cover 86 may be mounted on the second gantry 820. After the first cantilever 813 and the second cantilever 822 are connected, the lock cover 86 may be slided in such a way that the lock cover 86 covers the first cantilever 813 and the second cantilever 822. The lock cover 86 may be connected between the first bracket 814 and the second bracket 820, and the lock cover 86 is combined with the first bracket 814 and the second bracket 820 to cover the first cantilever 813 and the second cantilever 822.

Figure 28:
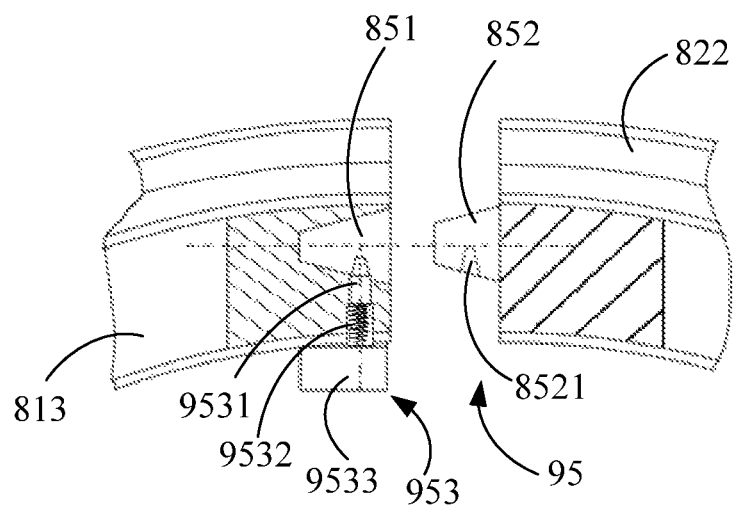
FIG. 28 is a schematic diagram illustrating an aligning and locking device of the imaging system 80 according to another example of the present disclosure.

FIG. 28 is a schematic diagram illustrating an aligning and locking device 95 according to another example of the present disclosure. The aligning and locking device 95 shown in FIG. 28 is similar to the aligning and locking device 85 shown in FIG. 25. Compared to the aligning and locking device 85 shown in FIG. 25, a locking member 953 of the aligning and locking device 95 shown in FIG. 28 may include a locking pin 9531, an elastic element 9532 (e.g. a spring) and a second electromagnet 9533. The locking pin 9531 is movably provided in one of the first cantilever 813 and the second cantilever 822 where the positioning groove 851 is located, and may be inserted into the locking groove 8521. In the illustrated example, the locking pin 9531 is movably provided in the first cantilever 813. The elastic element 9532 may be elastically provided on the bottom of the locking pin 9531. The second electromagnet 9533 may be provided on the bottom of the elastic element 9532 and may be energized to generate a magnetic force to attract the locking pin 9531, so as to compress the elastic element 9532.

In an example, when the first cantilever 813 and the second cantilever 822 are connected, the second electromagnet 9533 is energized to attract the locking pin 9531, in such a way that an end of the locking pin 9531 does not protrude into the locking groove 8521. When the first cantilever 813 and the second cantilever 822 are connected, the positioning block 852 is inserted into the positioning groove 851, the second electromagnet 9533 is de-energized, and the locking pin 9531 is pushed upward by an elastic force of the elastic element 9532 so that the locking pin 9531 may be inserted into the locking groove 8521, thereby locking ends of the first cantilever 813 and the second cantilever 822.

In another example, before the first cantilever 813 and the second cantilever 822 are connected, the elastic element 9532 supports the locking pin 9531 to protrude into the positioning groove 851. When the cantilever 813 and the second cantilever 822 are connected, the positioning block 852 may gradually protrude into the positioning groove 851 to press the locking pin 9531, so that the locking pin 9531 may be moved downward to deform the elastic element 9532. When the positioning block 852 completely occupies the positioning groove 851, the locking groove 8521 corresponds to the position of the locking pin 9531, and the locking pin 9531 is pushed to move upward by the elastic force of the elastic element 9532, so that the locking pin 9531 is inserted into the locking groove 8521, thereby locking the ends of the first cantilever 813 and the second cantilever 822.

When the first cantilever 813 and the second cantilever 822 are separated, the second electromagnet 9533 is energized to attract the locking pin 9531, so that the locking pin 9531 is retracted from the locking groove 8521.

The above description is merely examples of the aligning and locking device, and is not limited to the above examples. In another example, the locking member may include a locking pin that is inserted into the first cantilever and has a particular friction force with the first cantilever. The locking pin may be manually inserted into the locking groove 8521 to lock the first cantilever and the second cantilever, or pulled out of the locking groove 8521 to separate the first cantilever and the second cantilever.

The above aligning and locking device, the laser emitter and/or the lock cover and other components may also be applied to the imaging systems shown in FIG. 1, FIG. 4 to FIG. 8 and FIG. 14, and may also be applied to other imaging systems or medical devices, or may be applied to other components assembled together.

The foregoing disclosure is merely illustrative of preferred examples of the present disclosure but not intended to limit the present disclosure, and any modifications, equivalent substitutions, adaptations thereof made within the spirit and principles of the disclosure shall be encompassed in the scope of protection of the present disclosure.

For simplicity and illustrative purposes, the present disclosure is described by referring mainly to examples thereof. In the above descriptions, numerous specific details are set forth in order to provide a thorough understanding of the present disclosure. It will be readily apparent however, that the present disclosure may be practiced without limitation to these specific details. In other instances, some methods and structures have not been described in detail so as not to unnecessarily obscure the present disclosure. As used herein, the terms "a" and "an" are intended to denote at least one of a particular element, the term "includes" means includes but not limited to, the term "including" means including but not limited to, and the term "based on" means based at least in part on.

The above description is merely preferred examples of the present disclosure and is not intended to limit the present disclosure in any form. Although the present disclosure is disclosed by the above examples, the examples are not intended to limit the present disclosure. Those skilled in the art, without departing from the scope of the technical scheme of the present disclosure, may make a plurality of changes and modifications of the technical scheme of the present disclosure by the method and technical content disclosed above.

Therefore, without departing from the scope of the technical scheme of the present disclosure, based on technical essences of the present disclosure, any simple alterations, equal changes and modifications should fall within the protection scope of the technical scheme of the present disclosure. Accordingly, other embodiments are within the scope of the following claims.

What is claimed is:

1. An imaging device, comprising:
   a first cantilever;
   a second cantilever separably connected with the first cantilever; and
   an aligning and locking device provided at a connection of the first cantilever and the second cantilever, wherein the aligning and locking device comprises:
   a positioning groove provided on the first cantilever;
   a positioning block provided on the second cantilever and extendable into the positioning groove to cooperate with the positioning groove for positioning;
   a locking groove provided in the positioning block; and
   a locking member movably provided in the first cantilever and insertable into the locking groove to cooperate with the locking groove for locking;
   wherein
   the aligning and locking device also comprises:
   two first electromagnets provided on one of the first cantilever, the two first electromagnets mounted on both sides of the positioning groove, respectively, for attracting the second cantilever.

2. The imaging device of claim 1, wherein the locking member comprises:
   a locking screw with threads, wherein the locking screw is rotatably provided in the first cantilever.

3. The imaging device of claim 1, wherein the locking member comprises:
   a locking pin movably provided in the first cantilever and insertable into the locking groove; and
   an elastic element elastically provided on the bottom of the locking pin.

4. The imaging device of claim 3, wherein the locking member further comprises:
   a second electromagnet provided on the bottom of the locking pin and configured to be energized to generate a magnetic force for attracting the locking pin.

5. The imaging device of claim 1, further comprising:
   a laser emitter mounted on one of the first cantilever and the second cantilever, and
   a marking point provided on the other one of the first cantilever and the second cantilever and corresponding to the laser emitter.

6. The imaging device of claim 1, further comprising:
   a lock cover slidably provided outside the first cantilever and the second cantilever.

7. A medical apparatus, comprising:
   a first component;
   a second component configured to be assembled with the first component; and
   an aligning and locking device provided at a connection of the first component and the second component for aligning and locking the second component to the first component, wherein the aligning and locking device comprises:
   a positioning groove provided on the first component;
   a positioning block provided on the second component and extendable into the positioning groove to cooperate with the positioning groove for positioning;
   a locking groove provided in the positioning block; and
   a locking member movably provided in the first component and insertable into the locking groove to cooperate with the locking groove for locking;
   wherein
   the aligning and locking device also comprises:
   two first electromagnets provided on one of the first component, the two first electromagnets mounted on both sides of the positioning groove, respectively, for attracting the second component.

8. The medical apparatus of claim 7, wherein the locking member comprises:
   a locking screw with threads, wherein the locking screw is rotatably provided in the first component.

9. The medical apparatus of claim 7, wherein the locking member comprises:

a locking pin movably provided in the first component and insertable into the locking groove; and an elastic element elastically provided on the bottom of the locking pin.

10. The medical apparatus of claim 9, wherein the locking member further comprises:

a second electromagnet provided on the bottom of the locking pin and configured to be energized to generate a magnetic force for attracting the locking pin.

11. The medical device of claim 7, further comprising:

a laser emitter mounted on one of the first component and the second component, and a marking point provided on the other one of the first component and the second component and corresponding to the laser emitter.

12. The medical apparatus of claim 7, further comprising:

a lock cover slidably provided outside the first component and the second component.

13. An imaging device, comprising:

a first cantilever comprising a first guide wall;

a second cantilever separably connected with the first cantilever and comprising a second guide wall cooperating with the first guide wall, wherein the second guide wall is fitted to the first guide wall for guiding connection of the first cantilever and the second cantilever; and a locking member movably provided in the first guide wall and the second guide wall for locking the first cantilever and the second cantilever;

wherein further comprising:

two first electromagnets provided on one of the first cantilever, the two first electromagnets mounted on a side of the first guide wall and a side of the second guide wall, respectively, for attracting the second cantilever.

14. The imaging device of claim 13, wherein the locking member comprises:

a locking screw with threads, wherein the locking screw is rotatably provided in the first guide wall and the second guide wall.

15. The imaging device of claim 13, wherein the locking member comprises:

a locking pin; and an elastic element elastically provided on the bottom of the locking pin.

16. The imaging device of claim 15, wherein the locking member further comprises:

a second electromagnet provided on the bottom of the locking pin and configured to be energized to generate a magnetic force for attracting the locking pin.

17. The imaging device of claim 13, further comprising:

a laser emitter mounted on one of the first cantilever and the second cantilever, and a marking point provided on the other one of the first cantilever and the second cantilever and corresponding to the laser emitter.

* * * * *